United States Patent [19]

Voss et al.

[11] Patent Number: 4,550,163

[45] Date of Patent: Oct. 29, 1985

[54] LIGAND ANALOG-IRREVERSIBLE ENZYME INHIBITOR CONJUGATES

[75] Inventors: Houston F. Voss; Jacob Plattner, both of Libertyville; Thomas R. Herrin, Waukegan, all of Ill.

[73] Assignee: Abbott Laboratories, North Chicago, Ill.

[21] Appl. No.: 228,414

[22] Filed: Jan. 26, 1981

Related U.S. Application Data

[62] Division of Ser. No. 9,007, Feb. 5, 1979, Pat. No. 4,273,866.

[51] Int. Cl.$^4$ .............................. C07F 9/60; C07F 9/40
[52] U.S. Cl. .................................... 544/244; 260/944; 260/397.4; 260/397.5; 260/397.2; 536/13.6; 536/25; 548/413
[58] Field of Search .................. 260/944, 397.4, 397.5, 260/397.2, 457, 455 R; 544/244; 548/413; 536/13.6, 25

Primary Examiner—Anton H. Sutto

Attorney, Agent, or Firm—Martin L. Katz; Margaret M. O'Brien

[57] ABSTRACT

The present invention encompasses a method for determining ligands in test samples comprising intermixing with the test sample a ligand analog-irreversible enzyme inhibitor conjugate and a binding protein bindable to the ligand and the ligand analog-irreversible enzyme inhibitor conjugate and wherein the amount of ligand analog-irreversible enzyme inhibitor conjugate bound by the binding protein is related to the amount of ligand in the test sample, said binding protein inactivating the irreversible enzyme inhibitor when bound to the ligand analog portion of the conjugate; intermixing an enzyme which is irreversibly inhibited by the ligand analog-irreversible enzyme inhibitor conjugate unbound by the binding protein; and intermixing substrate to the enzyme and monitoring the enzyme substrate reaction.

The invention also includes ligand analog-irreversible enzyme inhibitor conjugates useful as reagents in practicing the method. Methods and reagents of the present are particularly useful in determining drugs, hormones, and the like in biological fluids.

25 Claims, No Drawings

LIGAND ANALOG-IRREVERSIBLE ENZYME INHIBITOR CONJUGATES

This is a division of application Ser. No. 9,007 filed Feb. 5, 1979 now U.S. Pat. No. 4,273,866.

BACKGROUND OF THE INVENTION

A variety of enzyme immunoassay techniques are known. These include methods wherein an enzyme is bound to an antibody or antigen to be detected. Competition between the enzyme labeled species and unknown for the binding partner bound to a solid support is measured. The enzyme remaining in the solution is measured by reaction to substrate.

Homogeneous enzyme immunoassay techniques are described in U.S. Pat. No. 4,043,872 (hapten bound to enzyme) and U.S. Pat. No. 4,065,354 (hapten bound to lysoyme). Enzyme cofactor labeled ligand are described in Analytical Biochemistry 72, 271 and 283 (1976). Derwendt Abstract B4, Natural Products Week A26, pp. 30 of DT2754-086 describes reversible binding enzyme modulators as a labeling substance for antigen, antibody, hormone, vitamins or drugs. Belgium Pat. No. 864,856, Sept. 9, 1978, describes conjugates using methotrexate as an enzyme inhibitor bound to ligand analogs.

Methods and reagents of the present invention are particularly distinct in that they involve the use of irreversible enzyme inhibitors conjugated to ligand analogs. The inhibitors of the present invention react with the enzymes forming covalent bonds altering the structure of the enzyme and thereby irreversibly inhibiting the enzyme activity. In particular, organophosphorous irreversible enzyme inhibitors which react with an enzyme to form covalent bonds are conjugated to ligand analogs.

SUMMARY OF THE INVENTION

The present invention encompasses a method for determining ligands in test samples comprising intermixing with the test sample a ligand analog-irreversible enzyme inhibitor conjugate and a binding protein bindable to the ligand and the ligand analog-irreversible enzyme inhibitor conjugate and wherein the amount of ligand analog-irreversible enzyme inhibitor conjugate bound by the binding protein is related to the amount of ligand in the test sample, said binding protein inactivating the irreversible enzyme inhibitor when bound to the ligand analog portion of the conjugate; intermixing an enzyme which is irreversibly inhibited by the ligand analog-irreversible enzyme inhibitor conjugate unbound by the binding protein; and intermixing substrate to the enzyme and monitoring the enzyme substrate reaction. The invention includes ligand analog-irreversible enzyme inhibitor conjugates useful as reagents in practicing the above method. The irreversible enzyme inhibitor portion of the conjugate reacts with the enzyme forming covalent bonds and thereby inactivating the enzyme. Methods and reagents of the present invention are particularly useful in determining drugs, hormones, and the like.

DETAILED DESCRIPTION OF THE INVENTION

The present invention relates to methods and reagents for determining ligands in biological fluids such as serum, plasma, spinal fluid, amnionic fluid and urine.

The term ligand as used in the present invention refers to haptens, polypeptides, proteins, and glycoproteins having molecular weights generally below 150,000.

Haptens are protein-free bodies, generally of low molecular weight that do not induce antibody formation when injected into an animal, but are reactive to antibodies. Antibodies to hapten are raised by first conjugating the hapten to a protein and injecting the conjugate product into an animal or human. The resulting antibodies are isolated by conventional antibody isolation techniques. For purposes of the present invention, the antibodies should be substantially free of serum protein materials such as indicator enzymes used in the test or inhibitors to antibody binding. These are conveniently removed by ion exchange chromatography on an anion exchange column or other suitable protein separation technique.

Representative ligands determinable by methods of the present invention are steroids such as estrone, estradiol, cortisol, testosterone, progesterone, chenodeoxycholic acid, digoxin, cholic acid, deoxycholic acid, lithocholic acids and the ester and amide derivatives thereof; vitamins such as vitamin B-12, folid acid; thyroxine, triiodothyronine, histamine, serotonin, prostaglandins such as PGE, PGF, PGA; adrenalin, noradrenalin and drugs such as opiates, theophylline, dilantin; barbituates such as phenobarbitol and derivatives thereof and carbamazepins, aminoglycoside antibiotics like gentimycin and tobramycin.

Representative polypeptides and glycoproteins determinable by methods of the present invention are insulin, platelet factor 4 and polypeptide determinants of large antigens.

Ligand analogs are functional or functionalized ligands suitable for conjugation to irreversible enzyme inhibitors. Acids, esters, amides, amines, hydroxy, isocyanate, isothiocyanate are suitable functional groups.

Representative enzymes and irreversible enzyme inhibitors useful for practicing the present invention are listed in Table I.

TABLE I

| Irreversible Inhibitor | Enzymes |
| --- | --- |
| Organophosphate triester | Trypsin |
| Organophosphonate diesters | Acetylcholinesterase |
| Organophosphothioates | Butyrlcholinesterase |
| | Chymotrypsin |
| | Thrombin |
| | Elastase |
| | Adenosine Deaminase |
| Alkylsulfonates | Acetylcholinesterase |
| Alkyl Isocyanates | Elastase |
| | Trypsin |
| | Chymotrypsin |
| Peptide Chloroketones | Trypsin |
| | Chymotrypsin |
| | Elastase |
| | Adenosine Deaminase |
| p-Chloromercuribenzoate Derivatives | Papain |
| | Alcohol Dehydrogenase |
| | Chymopapain |
| | Clostridiopeptidase B |
| | Adenosine Deaminase |
| | Lipase |
| | $\beta$-amalyase |
| | Pepsin |
| | Glyceraldehyde-3-phosphate Deh. |
| p-Chloromercuribenzoate Derivatives(Continued) | Luciferase |
| | Aspartate Aminotransferase |
| | Alanine Aminotransferase |
| | Hexokinase |

TABLE I-continued

| Irreversible Inhibitor | Enzymes |
| --- | --- |
| Substrate Epoxides | Pepsin |
| 6-diazo-5-oxo-L—norleucine Derivatives | Glutaminase A |
| Iodoacetic Acid Derivatives | Acid deoxyribonuclease II |
|  | Alcohol dehydrogenase |
| N—Bromosuccinimide Derivatives | Acid deoxyribonuclease II |
|  | Dextranase |

Organophosphorous irreversible enzyme inhibitors are preferred. J. Am. Chem. Soc., 80, 456, (1958); J. Am. Chem. Soc., 82, 596, (1960), and Rec. Trav. Chim., 86, 399, (1967) describe several classes of organophosphorous compounds which are suitable irreversible enzyme inhibitors. Preferred organophosphorous compounds useful for conjugation to ligand analogs are represented by the following formula:

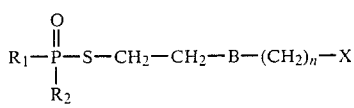

wherein B represents nitrogen or sulfur or their alkylated salts; n is 1-10, preferrably 2-8; X represents a functional group such as hydroxy, amino, carboxy, α-halomethylcarboxy wherein the halo is iodo, chloro, or bromo; $R_1$ and $R_2$ represent an alkyl radical having 1-10 carbon atoms or alkoxy having 1-10 carbon atoms. The alkyl radical may be substituted with nitro, halo, cyano, benzyl or similar substituents. Those skilled in organic chemistry will recognize a wide variety of equivalent structures for practicing the present invention.

Another preferred irreversible enzyme inhibitor radical is represented by the formula:

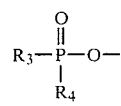

$R_3$ is the same as previously described for $R_1$ and $R_2$, and $R_4$ represents common organic leaving groups such as p-nitrophenyl, hydroxyquinolyl, as well as alkyl, halo, and cyano substituted quinolyls.

Irreversible enzyme inhibitors are bound to ligand analogs by conventional bifunctional bridging groups having the general formula:

X—A—Y wherein X and Y represent functional groups such as —OH, —NH$_2$, CO$_2$H(esters), —CO—CH$_2$Z, wherein Z is (I, Cl, Br). A represents —(CH$_2$)$_n$— wherein n is 3-20. The alkylene chain may be interupted with one or more bivalent groups such as —O—, —CO—, —S—, —NH—, —CONH—, —CH=CH—, —C≡C—, phenylene and sulfonium and ammonium salts. The alkylene chain may be substituted with common substituents such as halo (I, Br, Cl, F), hydroxy, cyano, phenyl, amino, carboxy, organo carboxyesters, alkyl having 1-7 carbon atoms, alkoxy having 1-3 carbon atoms. X—A—Y may be a small polypeptide or polysaccharide chain. Thus, X—A—Y is reacted by conventional techniques with an irreversible enzyme inhibitor and ligand analog to form amide, ester, amine, imine, sulfonamide, thioester, phosphate, thiophosphate and the like linkages between the bridging group and the irreversible enzyme inhibitor and ligand analog.

Most generally, a side chain is built on a ligand or ligand analog and the product reacted with an irreversible enzyme inhibitor suitably functionalized for reaction with the side chain on the ligand analog. Alternatively, a side chain is built on the irreversible enzyme inhibitor and reacted with a suitable ligand or ligand analog. Thus, compounds of the formula irreversible enzyme inhibitor-A-ligand analog are suitable reagents.

The following structures illustrate conjugates of the present invention.

Thyroxine

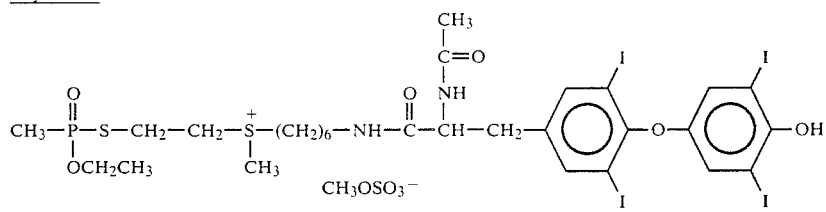

Cholic Acid

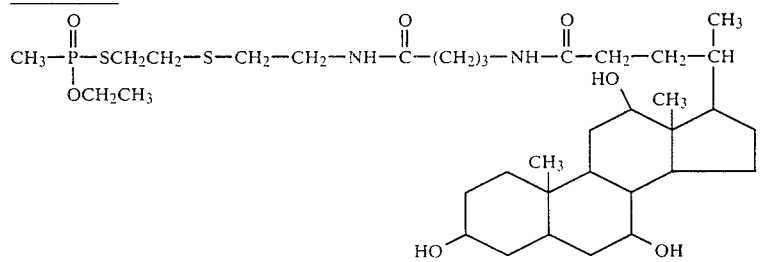

Dilantin

-continued
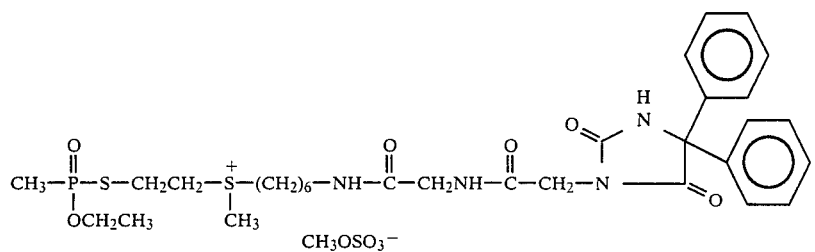
Digoxin
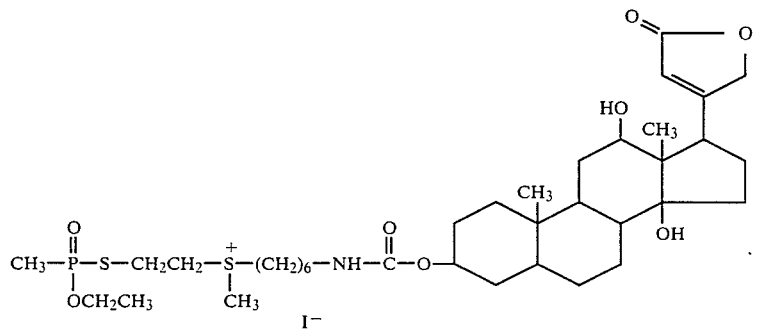
Theophylline
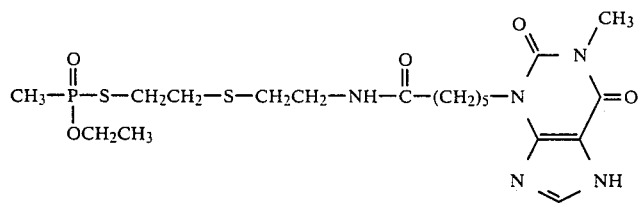
Cholic Acid
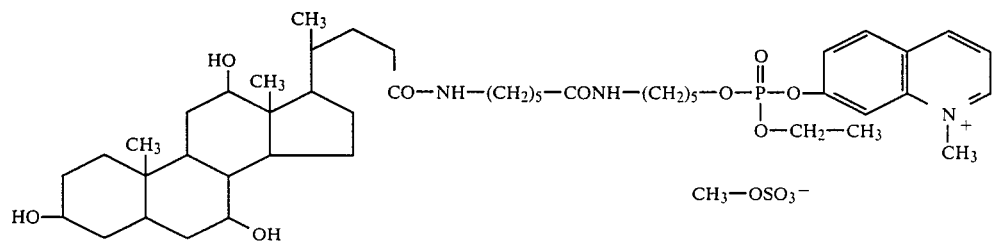
Digoxin
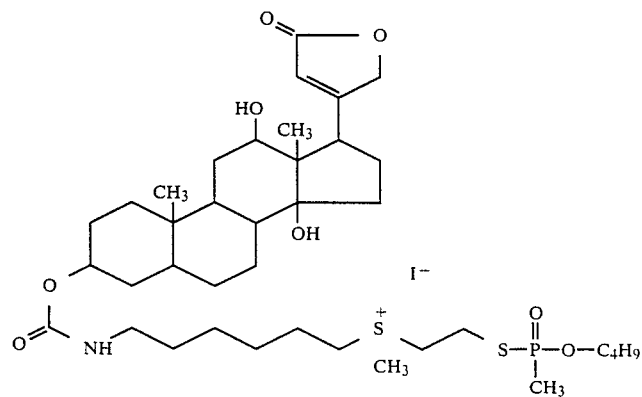
Digoxin -continued
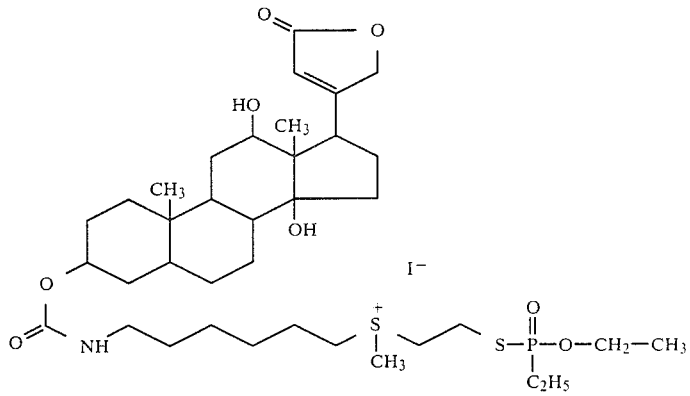
Folic Acid
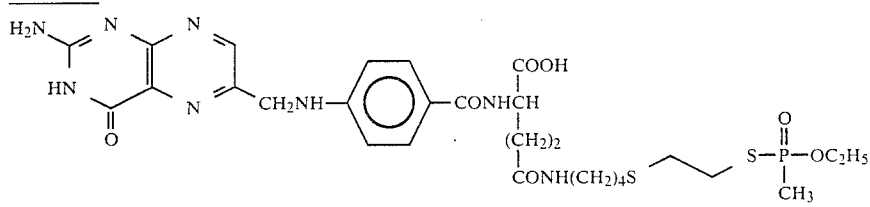
Methotrexate
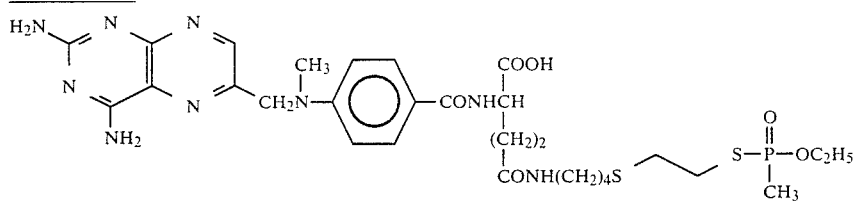
Cortisol
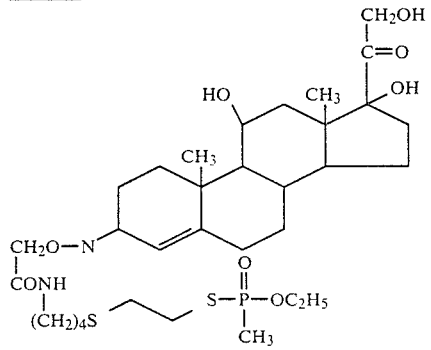
Valproic Acid
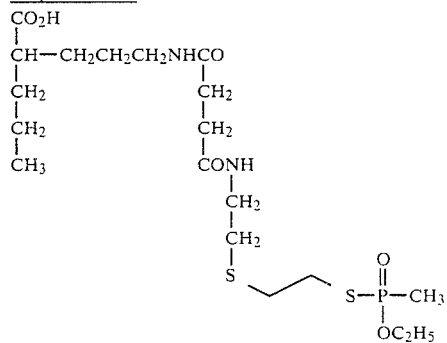
Sulfolithocholyl
Glycine

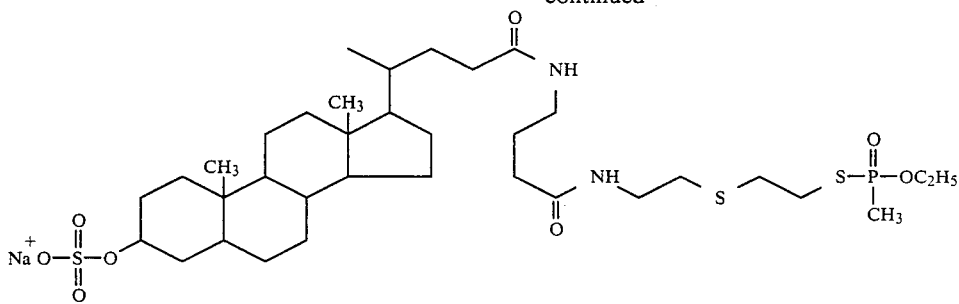

Lidocaine

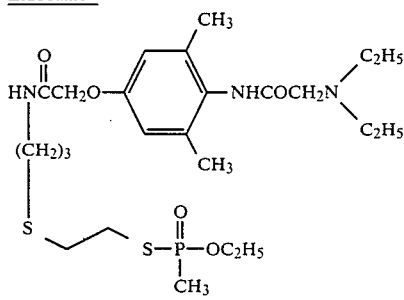

T₃

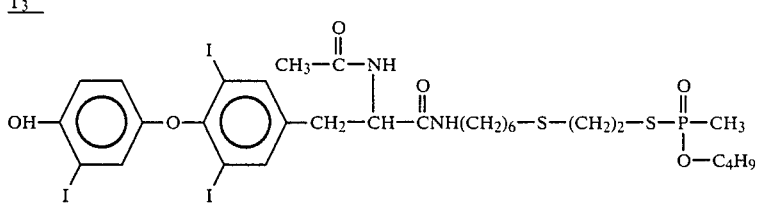

Gentamicin (bound to an amino group of gentamicin)—COCH₂CH₂CONHCH₂CH₂SCH₂CH₂—S—P(=O)(CH₃)(OC₂H₅)

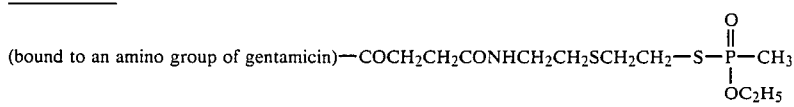

Tobramycin

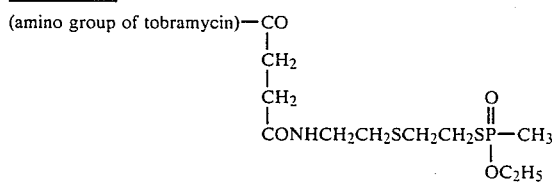

B₁₂

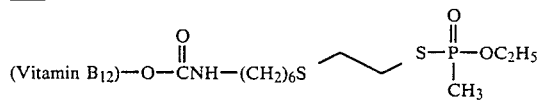

T₃

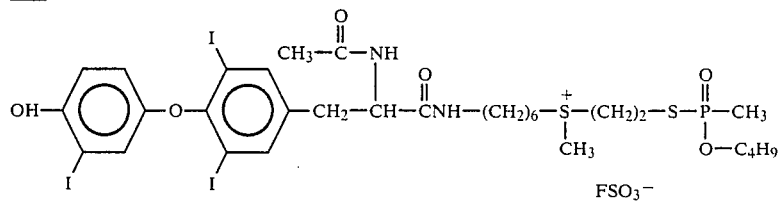

Binding proteins are antibodies or other specific binding proteins such as thyroid binding globulin which are bindable to the ligand to be determined and the ligand analog moiety of the ligand analog-irreversible enzyme inhibitor conjugate. When the binding protein is bound to the ligand analog the irreversible enzyme inhibitor is inactivated.

Reactions involved in the present invention are illustrated as follows:

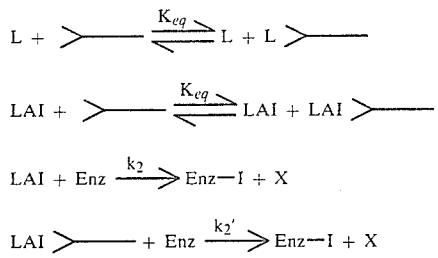

L (ligand)>—(binding protein); LAI (irreversible enzyme inhibitor-ligand analog conjugate); Enz (enzyme) Enz-I (inactivated enzyme); X (reaction by-product); $k_2 >> k_2'$ and in most cases $k_2'$ is reduced to being almost zero; i.e., the binding protein inactivates the LAI.

The reaction can be monitored by kinetic or endpoint techniques. Thus, $$\text{the reaction } -\frac{d\,\text{Enz}}{dt} = k_2[\text{LAI}][\text{Enz}]$$

is followed when using kinetic techniques. By using an excess of enzyme and allowing time for the reaction to go to 99% completion, this system is conveniently adapted to endpoint techniques.

Preferred conjugates for use in conjunction with acetylcholinesterase (E.C.3.1.1.7) are compounds of the formula:

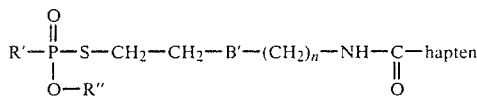

wherein R' and R" are alkyl having 1–10 carbon atoms, n is 2–8, and B' is —S— or the sulfonium salts thereof. The hapten is a carboxylic acid containing hapten or hapten modified to contain a carboxylic acid, both referred to herein as ligand analogs. The invention also includes the corresponding methyl sulfonium salts.

Most preferred conjugates are those in which R' and R" represent alkyl having 1–4 carbon atoms and n is 2–6 and including the sulfonium salts thereof. Especially preferred are compounds of the formula:

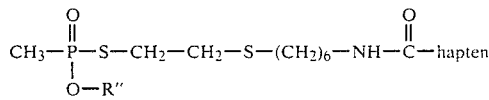

wherein R" is ethyl or n-butyl and the corresponding sulfonium salts such as

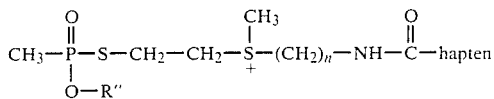

wherein the counter ion is iodide or methylsulfate or the like. Those skilled in the chemistry arts will recognize equivalence and interchangeability of a large variety of anions. Compounds in which n is 2–6 are also preferred.

Other compounds preferred for practicing this invention are:

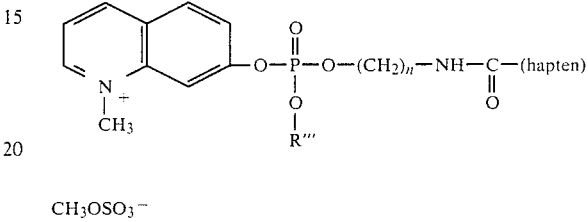

$$CH_3OSO_3^-$$

wherein R''' is alkyl having 1–10 carbon atoms preferably 1–4 and n is 1–12; and

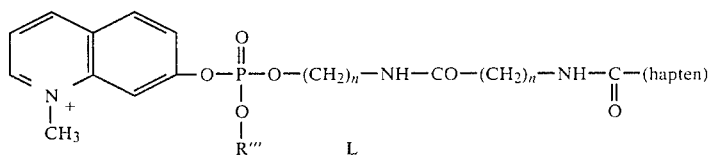

wherein R''' is alkyl having 1–10 carbon atoms preferably 1–4 and n is 2–8, and L is a biologically compatible counter ion such as methylsulfate, iodide and the like.

Thus, the present invention encompasses analytical reagents comprising irreversible enzyme inhibitors-ligand analog conjugates.

Operation of the present invention is illustrated by the following scheme:

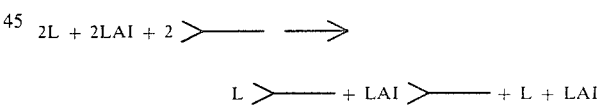

Thus, ligand (L) and ligand analog-irreversible inhibitor conjugate (LAI) compete with binding protein>—). Binding protein bound to (LAI) inactivates the inhibitor while free LAI is available to irreversibly inhibit the enzyme. The larger the amount of ligand present in the test sample, the lower the amount of LAI bound to the binding protein and, therefore, more enzyme will be inhibited by free LAI. The uninhibited enzyme is reacted with a suitable substrate and the enzyme substrate reaction monitored.

Colorimetric analysis are conveniently carried out on a bichromatic spectrophotometer described in U.S. Pat. Nos. 3,748,044; 3,831,618; 3,833,304; 3,900,289; 3,817,425; and 3,811,780.

Test samples can be pretreated to remove or inactivate interferring protein. Interferring proteins can be removed by precipitation with organic solvents such as ethanol, methanol and the like. Heat treatment at basic pH is also an effective way of eliminating interferring proteins. It is frequently desirable to further treat test samples with strong acid or base to separate the hapten to be tested from protein. In some cases, it is only necessary to specifically inactivate interfering proteins. For example, serum cholinesterase is specifically inhibited with specific inhibitors which have selective activity against serum pseudocholinesterase. Compounds with such activity are orphenidrine, N-methyl-orphenadrine, phenathiazines, bis-β-methylcholine ester of phthalic acid, quinoline, and artane and its alkyl quaternary salts.

Typically, digoxin in serum treated with N-methylorphenadrine is determined using the kinetic method of analysis and a compound of the formula:

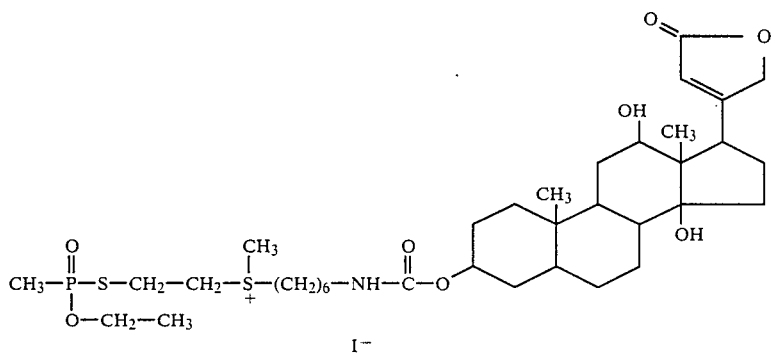

is used as an irreversible enzyme inhibitor-ligand analog conjugate to compete for digoxin antibody with digoxin in the test sample. After a brief incubation period, acetylcholinesterase is added. The uninhibited enzyme is measured by the reaction with acetylthiocholine liberating thiocholine. The liberated thiocholine is measured colorimetrically by further reaction with 5,5'-dithiobis(2-nitrobenzoic acid). This reaction is monitored at 412 nm. Standards are used to prepare a standard curve from which unknowns are determined.

Methods and reagents of the present invention are equally applicable for determining binding proteins such as antibodies. In this technique, the ligand analog binding partner to the binding protein to be determined is conjugated to an irreversible enzyme inhibitor. Binding proteins in test samples are determined by intermixing a ligand analog-irreversible enzyme inhibitor wherein the ligand analog moiety of the conjugate is specifically bindable to the binding protein to be determined, then intermixing an enzyme irreversibly inhibited by the irreversible inhibitor moiety of the conjugate, adding substrate to the enzyme and monitoring the reaction. Since the binding protein inactivates the irreversible enzyme inhibitor, the larger the amount of binding protein, the greater the enzyme activity.

The hereinafter set forth examples are intended to illustrate the invention and not to limit it in scope or spirit.

EXAMPLE I

To a solution of 6-aminocaproic acid (7.8 g) and 5.0 g of sodium bicarbonate in 50 ml of water is added by dropwise addition 16 g of N-benzyloxycarbonyloxysuccinimide in 60 ml of tetrahydrofuran. The mixture is stirred for one hour at room temperature and then the tetrahydrofuran is removed at reduced pressure. The residue is acidified to pH 3 and extracted with methylene chloride and dried over anhydrous magnesium sulfate. The magnesium sulfate is removed by filtration and the solvent is removed by evaporation. Recrystallization from ethyl acetate/hexane provides N-benzyloxycarbonyl-6-aminocaproic acid.

To a solution of 4.09 g of this compound in 40 ml of dioxane is added 2.3 g of N-hydroxysuccinimide and 4.12 g of dicyclohexylcarbodiimide. An additional 10 ml of dioxane is used to aid in reagent transfer. The mixture is stirred overnight at room temperature. The mixture is filtered and 2.06 g of 5-aminopentanol in 5 ml of water is added to the filtrate. The reaction mixture is stirred for one hour, concentrated at reduced pressure, and the residue extracted with methylene chloride. The extracts are washed with water and concentrated sodium chloride solution. The solution is dried over anhydrous magnesium sulfate. The magnesium sulfate is removed by filtration and the solvent is removed by evaporation at reduced pressure. The residue is crystallized twice from ethyl acetate to give N-(5-hydroxypentyl)-6-benzyloxycarbonylaminohexanamide, mp 92.5°-94° C.

This material, 4.0 g, is reduced with Pd/C in ethanol under low hydrogen pressure. The catalyst is removed by filtration and the solvent evaporated under reduced pressure to provide N-(5-hydroxypentyl)-6-aminohexanamide.

To a solution of 12-acetyloxy-3-chloroformyloxy-14-hydroxycard-20(22)enolide derivative of digoxigenin (U.S. Pat. No. 3,981,982) in 40 ml of dioxane is added 575 mg of N-hydroxysuccinimide. The mixture is cooled in a cold water bath and 0.695 ml of triethylamine added. The mixture is stirred at room temperature for three hours. The mixture is filtered and the filtrate is added to a solution of 973 mg of N-(5-hydroxypentyl)-6-aminohexanamide and 378 mg of sodium bicarbonate in 20 ml of water and 10 ml of ethanol. After one hour, the solvent is evaporated at reduced pressure and the residue dissolved in methylene chloride. The methylene chloride solution is washed with water, saturated sodium chloride solution and dried over anhydrous magnesium sulfate. The magnesium sulfate is removed by filtration on the solvent by evaporation at reduced pressure. The residue is chromatographed on silica gel (200 g).

Elution with 5-15% methanol in methylene chloride provides 12-acetyloxy-3-[N-(12-hydroxy-6-oxo-7-azadodecyl)carbamoyloxy]-14-hydroxycard-20(22)enolide having the formula:

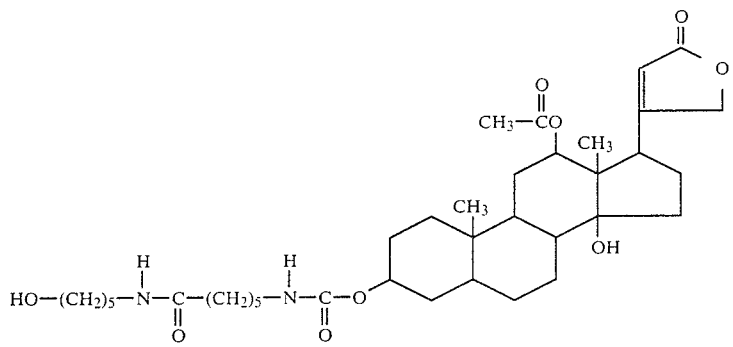

The above compound, 2.70 g, is dissolved in 50 ml of methanol and 50 ml of water is added and followed by the addition of 10 ml of triethylamine. The reaction mixture is allowed to stand at room temperature overnight. The solvent is evaporated at reduced pressure and the resulting residue chromatographed on a column of 150 g of silica gel and eluted with 2 liters of 10% methanol methylene chloride, to provide 3-[N-12-hydroxy-6-oxo-7-azadodecyl]carbamoyloxy]-14-hydroxycard-20(22)enolide.

A solution of 170 mg of triethylammonium ethyl-7-quinolyl phosphate in 10 ml of water is passed through 15 ml of sulfonic acid resin in the pyridinium form. The solution is concentrated at reduced pressure and dry pyridine evaporated from the residue. To this residue is added 253 mg of 3-[N-(12-hydroxy-6-oxo-7-azadodecyl)carbamoyloxy]-14-hydroxycard-20(22)enolide. Dry pyridine is evaporated from the residue three times. The residue is dissolved in 1.0 ml of dry pyridine and 145 mg of crystallized tris-isopropylbenzenesulfonyl chloride is added. The reaction mixture is stirred at room temperature for 15 hours. Ice is added and after 0.5 hours the mixture is extracted with methylene chloride. The methylene chloride solution is washed with water, saturated sodium bicarbonate, saturated sodium chloride and dried over anhydrous magnesium sulfate. The solvent is evaporated and toluene evaporated several times from the residue to remove the pyridine. The residue is chromatographed on silica gel using 5-10% methanol in methylene chloride as eluent, to provide a compound of the formula:

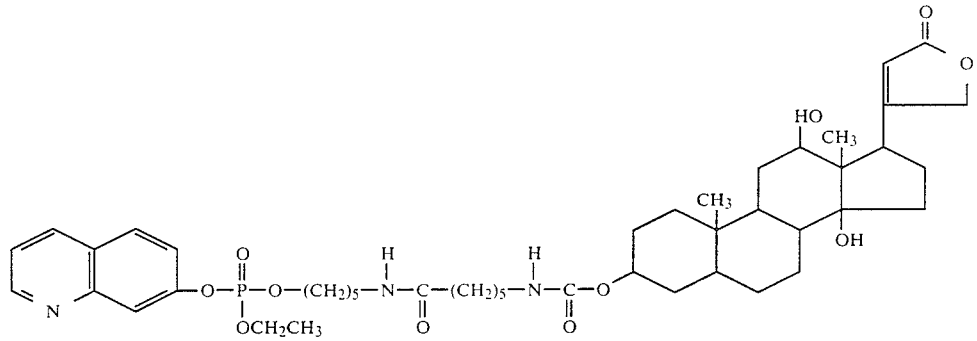

The above compound, 100 mg, and 23 μl of dimethylsulfate are dissolved in 0.50 ml of acetone and after four hours an additional 60 μl of dimethylsulfate in 2 ml of acetone are added and the mixture is allowed to stand overnight. The acetone solution is added to ethyl ether to give a white precipitate which is a compound of the formula

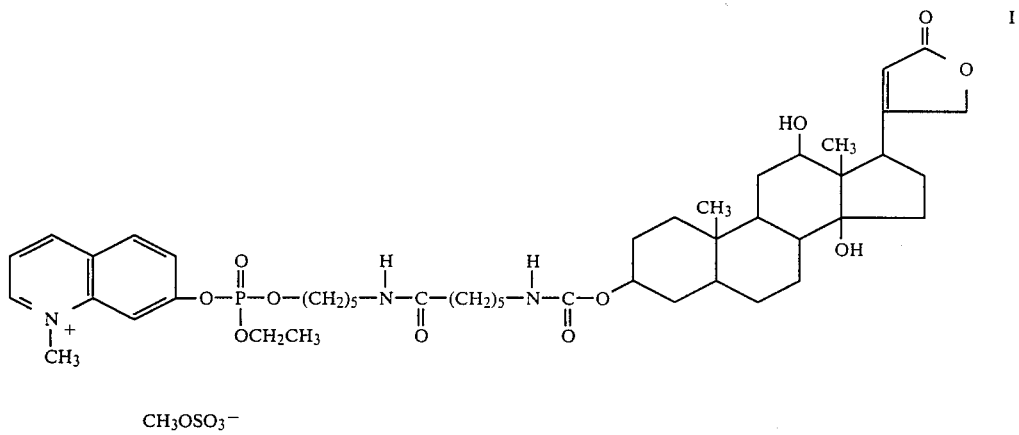

$CH_3OSO_3{}^-$

Antibody Modulation of Compound I Inhibitory Activity

A stock solution of Compound I ($4.6 \times 10^{-3}$ molar in methanol) is diluted 200-fold with pH 7.0, 0.1 molar phosphate buffer containing 0.1% gelatin. Digoxin antibody is diluted in phosphate-gelatin buffers as indicated in Table I. Fifty microliters of phosphate-gelatin buffer, pH 7.0, containing the indicated concentration of antibody is placed in sample cups of a bichromatic spectrophotometer (model ABA-100 ® sold by Abbott Laboratories). To each of these 50 μl is added 1 μl of Compound I working solution making the final concentration $4.5 \times 10^{-7}$ molar. The antibody and Compound I (inhibitor) are allowed to incubate for 10–15 minutes at room temperature. Each sample receives 1 μl of working enzyme solution ($9.5 \times 10^{-9}$ molar of E.electricus acetylcholinesterase in pH 7.0 phosphate-gelatin buffer). The final enzyme concentration is $1.9 \times 10^{-10}$ molar. The sample is diluted 1/26 with assay buffer containing acetylthiocholine, as substrate, $5 \times 10^{-4}$ molar and 5,5'-dithiobis(2-nitrobenzoic acid) (DTNB), $1.6 \times 10^{-4}$ molar in pH 7.0 phosphate-gelatin buffer. The change in absorbance with time is measured after 5 minutes in the bichromatic analyzer equipped with a 415/550 nm filter at 30° C. The results are as follows:

TABLE I

| Enzyme (M) | Antibody (M) | Compound I (M) | ΔAd/5 min. After Incubation Time | | |
|---|---|---|---|---|---|
| | | | 10' | 21' | 43' |
| $1.9 \times 10^{-10}$ | 0 | 0 | 0.220 | 0.221 | 0.222 |
| $1.9 \times 10^{-10}$ | $9 \times 10^{-7}$ | $4.5 \times 10^{-7}$ | 0.161 | 0.137 | 0.107 |
| $1.9 \times 10^{-10}$ | $9 \times 10^{-7}$ | $4.5 \times 10^{-7}$ | 0.086 | 0.027 | 0.005 |
| $1.9 \times 10^{-10}$ | 0 | $4.5 \times 10^{-7}$ | 0.045 | 0.015 | 0.003 |

The above experiment is repeated except digoxin at a concentration of $2.5 \times 10^{-5}$ molar is added to the sample cups. In this manner specific modulation is demonstrated. Fifty microliters of phosphate-gelatin buffer is added to a sample cup. The buffer solution either contains $2.5 \times 10^{-5}$ molar digoxin or is a control. To the sample cup is added a final concentration of $9 \times 10^{-7}$ molar digoxin antibody and $4.5 \times 10^{-7}$ molar Compound I. These solutions are allowed to incubate for 15 minutes and then enzyme is added and assayed according to the previous procedure. The results are as follows:

| Incubation Mixture | ΔAd/5 min. After Enzyme-Inhibitor Incubation Time | | |
|---|---|---|---|
| | 0.3' | 11' | 19' |
| Enzyme only (control) | 0.174 | 0.169 | 0.167 |
| Enzyme + Compound I | 0.162 | 0.037 | 0.013 |
| Enzyme + Compound I + Antibody | 0.160 | 0.129 | 0.115 |
| Enzyme + Compound I + Antibody + Digoxin | 0.160 | 0.068 | 0.038 |

Using the above procedures with the exception that the antibody final concentration in the sample is $4.5 \times 10^{-7}$ molar, various phosphate-gelatin buffer solutions are prepared with the indicated digoxin concentration. Each of these solutions are analyzed by adding antibody and Compound I to the solution as in the previous procedure, allowing a 2.5 minute incubation period to elapse and assaying for the residual enzyme activity after 21 minutes.

| μ M Digoxin | % Activity of Enzyme |
|---|---|
| 0.062 | 65% |
| 0.125 | 65% |
| 0.25 | 62% |
| 0.5 | 57% |
| 1.0 | 36% |

Normal human serum containing digoxin concentrations listed in the table below are assayed by the procedure set out above.

N,N,N-Trimethyl-2-(o-methyl-α-phenylbenzyloxy)ethylammonium methylsulfate(N-methylorphenadrine) prepared by reacting N,N-dimethyl-2-(o-methyl-α-phenylbenzyloxy)ethylamine(orphenadrine) with dimethylsulfate. At 1 mM concentration, this compound inhibits greater than 99% of human serum cholinesterase while inhibiting only 25% of cholinesterase from E.electricus.

N-Ethylmaleimide is used to block background sulfhydryl groups in human serum.

Thus, 1 μl of concentrated digoxin antibody in pH 7.0 phosphate-gelatin buffer containing 50 mM of N-methylorphenadrine is added to 50 μl of each serum standard then N-ethylmaleimide is added with mixing to each serum standard to make a working concentration of 1.6 mM. To the serum is also added 1 μl of a solution containing Compound I in pH 7.0, 0.1 molar phosphate-gelatin buffer. The final antibody concentration is $8.0 \times 10^{-7}$ molar and the final concentration of Compound I is $4.5 \times 10^{-7}$. These solutions are allowed to incubate for 12 minutes at which time acetylcholinesterase is added as before. After 26 minutes, the bichromatic spectrophotometer is started and a sample from each cup is diluted 26-fold with assay buffer containing $1.6 \times 10^{-5}$ molar DTNB, $5 \times 10^{-4}$ molar acetyl-β-methylthiocholine iodide, and 1 mM N-methylorphenadrine in pH 7.0, 0.1 molar phosphate-gelatin buffer. The final enzyme concentration is about $2 \times 10^{-11}$ molar and the cuvette temperature is 30° C. The change in absorbance after 5 minutes is as follows:

| Digoxin in Serum (μM) | ΔAd/5 min. |
| --- | --- |
| 0.1 | 0.096 |
| 0.13 | 0.089 |
| 0.17 | 0.083 |
| 0.26 | 0.077 |
| 0.34 | 0.073 |
| 0.51 | 0.063 |
| 0.64 | 0.060 |
| 0.85 | 0.047 |
| 1.30 | 0.035 |

EXAMPLE II

Cholic acid, 4.08 g, is dissolved in 10 ml of dry dimethylformamide and 3.40 g of imidazole is added, followed by 3.60 g of t-butyldimethylsilyl chloride. The reaction mixture is allowed to stand overnight at room temperature. The reaction mixture is poured into water, filtered and the precipitate is washed with water. This precipitate is dissolved in 30 ml of tetrahydrofuran and 3 ml of water and 2 ml of acetic acid is added. After 6.5 hours, the solvent is evaporated and the residue chromatographed on 200 g of silica gel with 5% methanol in methylene chloride as eluent, to provide 3α-(t-butyldimethylsilyloxy)-7α,12α-dihydroxy-5β-cholan-24-oic acid, mp 145.5°–148, having the following structural formula:

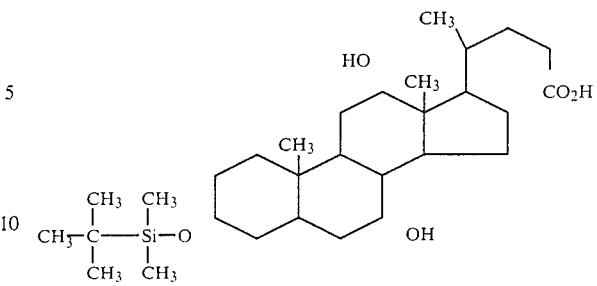

The above compound, 2.092 g, 1.728 g of N-(5-hydroxypentyl)-6-aminohexanamide and 1.87 g of N-ethoxycarbonyl-2-ethoxy-1,2-dihydroquinoline were refluxed in 175 ml of ethyl acetate for 24 hours. The reaction mixture is allowed to stand at room temperature to give a crystalline compound. This material is recrystallized from ethyl acetate to give 260 mg of 3α-(t-butyldimethylsilyloxy)-7α,12α-dihydroxy-N-[12-hydroxy-6-oxo-7-azadodecyl]cholan-24-amide, mp 145.5°–148° C., having the following structural formula:

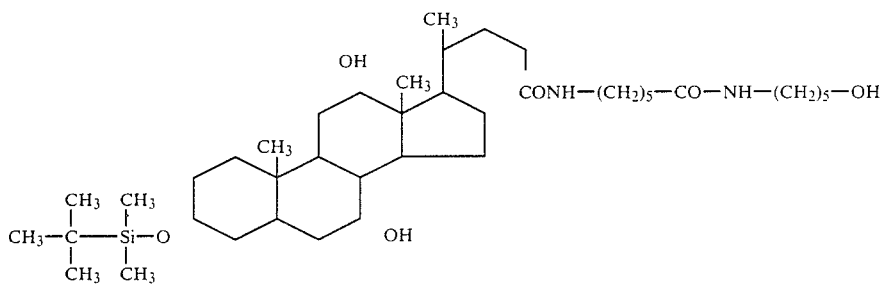

A solution of 424 mg of triethylammonium ethyl-7-quinolyl phosphate in 10 ml of water is passed through 15 ml of sulfonic acid resin in the pyridinium form. The eluent is concentrated at reduced pressure and dry pyridine evaporated from the residue two times. To the residue is added 721 mg of the above alcohol. Dry pyridine is evaporated from the residue three times. The residue is dissolved in 1.0 ml of dry pyridine and 364 mg of crystallized tris-isopropylbenzenesulfonyl chloride is added.

The reaction mixture is stirred at room temperature for 15 hours. Ice is added and after 0.5 hours the mixture is extracted with methylene chloride. The methylene chloride solution is washed with saturated sodium bicarbonate and saturated sodium chloride solution and dried over anhydrous magnesium sulfate. The solvent is evaporated and toluene evaporated several times from the residue to remove pyridine. The residue is added to a column of 50 g of silica gel and the column washed with 300 ml of 5% methanol-methylene chloride and 1000 ml of 10% methanol-methylene chloride. The solvent is removed to provide a compound of the formula:

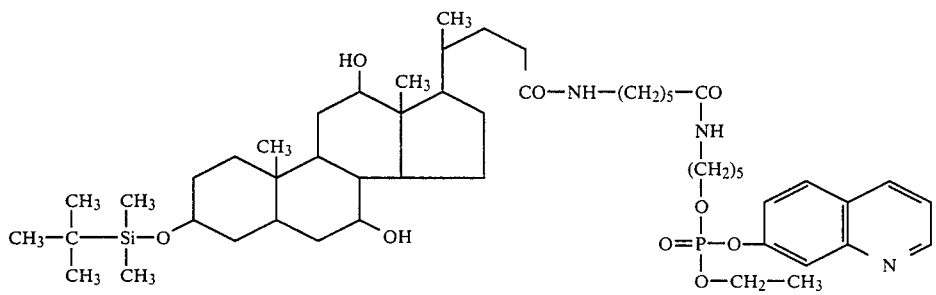

This compound, 40 mg, is dissolved in 2 ml of acetone and 0.10 ml of dimethylformamide followed by 40 μl of dimethylsulfate. The reaction mixture is allowed to stand at room temperature overnight. The acetone mixture is added to ethyl ether and the mixture centrifuged. The precipitate is triturated with ethyl ether to give Compound II of the formula:

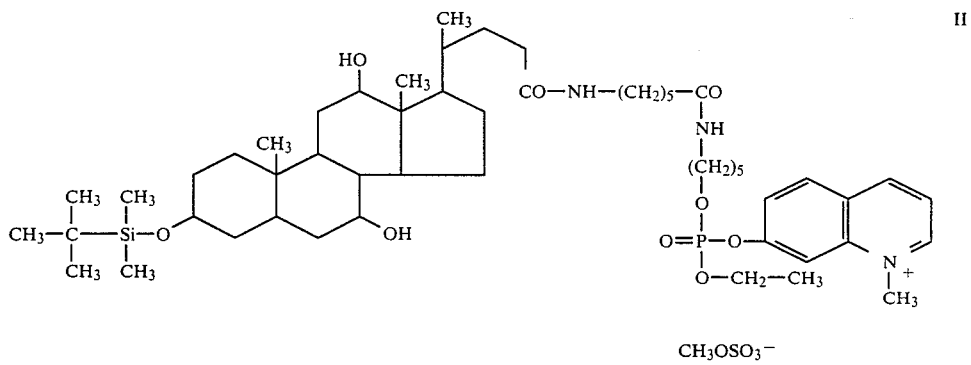

$CH_3OSO_3^-$

Compound II is used to demonstrate antibody modulation of inhibition and reversal by cholylglycine (glycocholic acid). Antibody against cholylglycine-bovine serum albumin (BSA) conjugates were raised in rabbits, and the rabbit serum obtained by conventional techniques. The anti-cholylglycine IgG fraction was obtained by ammonium sulfate fractionation and ion exchange chromatography. The concentration of antibody was not determined but was adjusted from a pooled fraction from the ion exchange column to give best modulation of inhibition by Compound II. In a control experiment, IgG against digoxin purified in an identical manner as the anticholylglycine IgG showed no effect on activity of the inhibition indicating a specific binding of Compound II. The experiment is carried out on an ABA-100® model bichromatic analyzer (Abbott Laboratories, North Chicago, Ill.) and the following settings were used:

| | | |
|---|---|---|
| Filter: | 415/550 nm | 2 minute offset |
| Temp. | 30° C. | Course Scale: 1 |
| Rate mode: | ~ | Carousel Rev.: 2 |
| Zero | 0.000 | Analysis Time: 5 min. |
| Calibrate: | 0.005 | 1/26 dilution plate |
| FRR: | On | |

The substrate solution and buffer are placed in the primary syringe of the dilution plate. The buffer is pH 7.0, 0.1M potassium phosphate, 0.1% gelatin. The substrate is acetylthiocholine at $5.0\times10^{-1}$M with DTNB at $1.6\times10^{-4}$M as indicator. The following table shows the reactant in the sample cup. In all cases, the acetylcholinesterase (*T.californica*) concentration is approximately $2\times10^{-10}$M and Compound II, the inhibitor, concentration is $10\times10^{-7}$M. Where cholyglycine is added, the concentration in the sample cup is $10^{-3}$M. The sample cup contains pH 7.0, 0.1M potassium phosphate buffer containing 0.1% gelatin plus the indicated components in the table:

Change in Ad in 5 Minutes as a Function of Time and Reaction Components

| Reaction Components | Enzyme-inhibitor Incubation Time (Min) T = 0 | Ad/5 Min. T = 13 | T = 25 | T = 36 |
|---|---|---|---|---|
| E alone | 246 | .237 | .234 | .230 |
| E + I | .226 | .072 | .025 | .013 |
| E + I + Ab | .235 | .192 | .164 | .147 |
| E + I + Ab + CG | .224 | .078 | .032 | .017 |
| E + Ab | .224 | .225 | .218 | .215 |
| E + Ab + CG | .225 | .223 | .216 | .207 |
| E + CG | .236 | .228 | .220 | .211 |
| E + I + CG | .224 | .062 | .022 | .013 |
| buffer alone | .001 | .003 | .001 | .002 |

E = acetylcholinesterase
I = Compound II
CG = cholylglycine
Ab = antibody to cholylglycine conjugated to BSA

EXAMPLE III

Into 100 ml of tetrahydrofuran is added successively 17.0 g of N-(t-butoxycarbonyl)-4-aminobutyric acid prepared by the procedure of Moreder et al.; Z. Physiol. Chem., 357, 1651 (1976), 10.6 g of N-hydroxysuccinimide, and 18.9 g of dicyclohexylcarbodiimide. The mixture is then stirred for 2 hours. The resulting dicyclohexylurea is filtered and 11.1 g of 5-amino-3-thia-1-pentanol in 150 ml of tetrahydrofuran is added to the filtrate. After stirring for 2.5 hours, the tetrahydrofuran is evaporated and the residue partitioned between methylene chloride and brine. The methylene chloride fraction is washed with saturated aqueous sodium bicarbonate, dried, and the solvent removed to provide an oil, which is 10-(t-butoxycarbamoyl-7-oxo-6-aza-3)-thiadecanol having the formula:

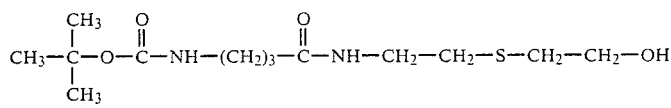

Under an inert atmosphere, 2.28 g of this compound, 1.45 g of diisopropylethylamine and 1.8 g of methanesulfonic anhydride are successively added to 20 ml fo methylene chloride at 0° C. After 30 minutes, 2.0 g of O-ethyl methylphosphonothioate and 1.92 g of diisopropylethylamine are added to the reaction mixture. The solution is allowed to warm to room temperature and then heated at 45° C. for 1.5 hours. The solution is partitioned between brine and methylene chloride and washed successively with 5% hydrochloric acid, saturated sodium bicarbonate and then dried over anhydrous magnesium sulfate. The magnesium sulfate is filtered and the solvent evaporated to provide a yellow oil which is O-ethyl-S-[10-(t-butoxycarbamoyl)-6-aza-7-oxo-3-thiadecyl]methylphosphonothioate, having the formula:

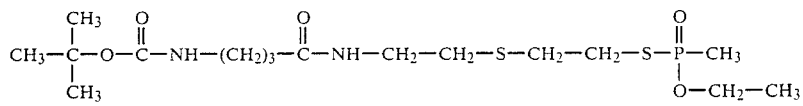

At room temperature 1.0 g of this compound is dissolved in 4 ml of 50% trifluoroacetic acid in methylene chloride and the mixture is stirred for 10 minutes. The solvent is evaporated under reduced pressure and the residue dissolved in an excess of benzene. The benzene is rapidly distilled so that traces of trifluoroacetic acid are removed. The residual oil is then dissolved in 2 ml of dimethylformamide and 1.08 g of the succinimide active ester of cholic acid and 37 mg of hydroxybenzotriazole are added successively. The pH of the solution is adjusted to 7.5 with triethylamine. After stirring for 6 hours, the solvent is removed by evaporation under reduced pressure and the residue is partitioned between brine and methylene chloride. The methylene chloride fraction is washed with saturated sodium bicarbonate and dried over anhydrous magnesium sulfate. The magnesium sulfate is filtered and the solvent removed by evaporation to provide N-[5-aza-10-ethoxymethylphosphinylthio-4-oxo-8-thiadecyl]-3α,7α,12α-trihydroxy-5β-cholan-24-amide having formula III:

The following reagents are used:
Buffer: Working solutions of all reagents are prepared in 0.1M sodium phosphate, pH 7.0 buffer, containing 0.1% gelatin (phosphate-gel).
Ligand Analog-Irreversible Inhibition Conjugate Solution: A working solution of $6.7 \times 10^{-6}$M solution of Compound III in phosphate-gel buffer is prepared by dilution from a 0.067M stock solution of Compound III in methanol.

Acetylcholinesterase: A working solution of 100 units acetylcholinesterase per ml is prepared in phosphate-gel buffer. One unit of enzyme activity is defined as the amount of enzyme which will catalyze the hydrolysis of one micromole of acetylcholine per minute at 25° C. Assuming a turnover number of $5 \times 10^5$ min.$^{-1}$, the concentration of enzyme in this solution is $2 \times 10^{-7}$M.

Substrate: In each case, enzyme activity is measured in phosphate-gel buffer containing $4.88 \times 10^{-4}$M acetylthiocholine and $1.56 \times 10^{-4}$M DTNB.

The pseudo-first order rate constant for the inhibition reaction is measured by mixing 10 μl of the working conjugate solution with 500 μl phosphate-gel buffer. At time zero, 5 μl (0.5 units) acetylcholinestearate solution is added, vortexed, and incubated at room temperature. At periodic intervals, the amount of enzyme activity remaining is measured by withdrawing a 10 μl aliquot, mixing it with 1.0 ml substrate solution, and measuring the rate of increase in absorbance at 410 nm (ΔA/Δt) in a Varian Super Scan 3 spectrophotometer. The estimated pseudo-first order rate constant ($k_{1(est.)}$) is calculated according to equation 1:

$$k_{1(est.)} = - \frac{\ln \frac{(\Delta A/\Delta t)t_2}{(\Delta A/\Delta t)t_1}}{t_2 - t_1}$$

where $t_2$ and $t_1$ are the times after addition of enzyme at which the remaining activity (ΔA/Δt) is measured. The estimated second order rate constant for the inhibition reaction is then calculated by dividing $k_{1(est.)}$ by the concentration of the conjugate in the reaction

III

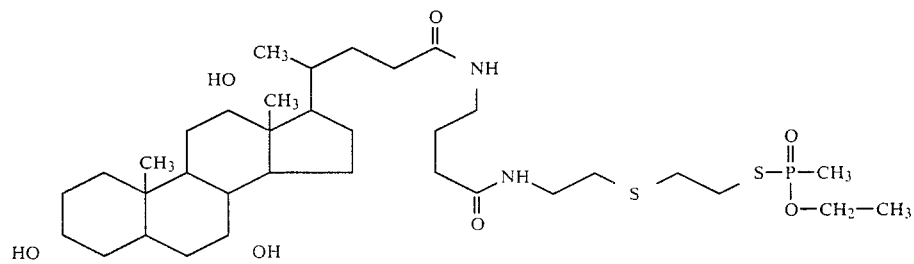

A. The rate constant for the inhibition of acetylcholinesterase by Compound III is estimated as follows:

($1.3 \times 10^{-7}$M). The values obtained by this method are shown in the following table:

TABLE

| Time (Minutes) | Activity (Absorbance Units per minute) |
|---|---|
| 0.5 | $9.45 \times 10^{-4}$ |
| 2.5 | $6.87 \times 10^{-4}$ |
| 5.0 | $4.87 \times 10^{-4}$ |

A plot of -ln activity versus t gives a slope of 0.147 min.$^{-1}$ as the pseudo-first order rate constant with a correlation coefficient of 0.998. The calculated apparent second order rate constant is then $1.1 \times 10^6$ liters mole$^{-1}$min$^{-1}$. Measurement can also be made on a bichromatic sprectrophotometer.

B. The utility of using acetylcholinesterase and Compound III as reagents to determine cholylglycine concentration is demonstrated as follows:

The following reagents are used:

Cholylglycine standards (buffer): Solutions of cholylglycine are prepared in 0.1M sodium phosphate buffer at pH 7.0 containing 0.1% gelatin at concentrations of $10^{-3}$, $10^{-4}$, $10^{-5}$, $10^{-6}$, and $10^{-7}$M. The standard solutions are prepared from a stock solution of 0.01M sodium glycocholate in water.

Anticholylglycine antibody: The IgG fraction of rabbit antiserum is prepared by mixing equal parts of a saturated solution of ammonium sulfate and the serum. The resulting precipitate is obtained by centrifugation and dialyzed versus 0.02M potassium phosphate at pH 8.0. The dialysate is then filtered and chromatographed on a DEAE cellulose column equilibrated in 0.02M potassium phosphate at pH 8.0. The working solution of antibody is obtained by pooling the appropriate fractions as determined by the elution profile. A Scatchard analysis of this solution indicated two classes of antibodies with binding constants of $1 \times 10^7$ and $1 \times 10^6$M$^{-1}$ with corresponding binding capacities of $2.2 \times 10^{-6}$ and $3.2 \times 10^{-5}$M.

Solutions of Compound III, acetylcholinesterase and substrate are prepared in a similar manner to those described above in part A of this example.

To measure the concentration of cholylglycine in phosphate-gel buffer, 96 μl phosphate-gel buffer, 20 μl of the appropriate cholylglycine solution, 4 μl of a $3.35 \times 10^{-6}$M solution of Compound III and 16 μl of the anticholylglycine antibody solution are combined in the sample cup of the bichromatic kinetic analyzer. The reagents are added in the order listed. Ten μl of silicon oil is then added to prevent evaporation. After a five minute incubation at room temperature, the bichromatic kinetic analyzer is turned on so that the carousel of sample cups will advance through the normal five minute revolution. As each sample cup arrives at the sampling position, 4 μl (0.09 units) in acetylcholinesterase solution is added. The final concentrations are $9.6 \times 10^{-8}$M Compound III, $1.67 \times 10^{-4}$ to $1.67 \times 10^{-8}$M cholylglycine, and $5.7 \times 10^{-10}$M acetylcholinesterase. After a 12 minute incubation, the amount of remaining enzyme activity is measured by delivering a 10 μl aliquot to the bichromatic kinetic analyzer cuvette (37° C.) and mixing it with 250 μl substrate solution. The 26-fold dilution of the material from the sample cup serves both to effectively stop the inhibition reaction and to dilute the enzyme into a concentration range where its activity could be easily measured. Enzyme activity is indicated by the difference between the absorbances (Ad) produced in five minutes at 415 nm and 550 nm. The results are shown in the following table:

| Cholylglycine (M) | Ad*/5 Min. |
|---|---|
| $1.67 \times 10^{-8}$ | $0.499 \pm 0.013$ |
| $1.67 \times 10^{-7}$ | $0.453 \pm 0.025$ |
| $1.67 \times 10^{-6}$ | $0.300 \pm 0.011$ |
| $1.67 \times 10^{-5}$ | $0.143 \pm 0.002$ |
| $1.67 \times 10^{-4}$ | $0.103 \pm 0.001$ |

*Ad is defined in the text. The values are the means ± one standard deviation. Each value represents replicates of three.

Cholylglycine concentrations in serum are determined in a manner similar to that described in the previous examples. For the purpose of this experiment standard serum solutions of cholylglycine are prepared by dilution of a 0.01M aqueous solution of sodium glycocholate into normal human serum, which has an endogenous cholylglycine concentration of $7.5 \times 10^{-7}$M, as determined by radioimmunoassay (Abbott Laboratories' CGRIA Kit). The total concentration of cholylglycine in the serum solutions are listed in the following table. All other solutions are the same as described in A and B above, except that the substrate solution contains 1.0 mM per liter of N-methyl orphenadrine to inhibit serum pseudocholinesterase.

To the sample cups of the bichromatic analyzer are added, in order, 39 μl phosphate-gel buffer, 6 μl of the appropriate normal human serum standard cholylglycine solution, 2 μl of a $3.35 \times 10^{-6}$m solution of Compound III, 8 μl of the anticholylglycine antibody solution, and 10 μl silicon oil. After a five minute incubation at room temperature, 5 μl (0.05 units) of acetylcholinesterase is added as described in Part B of this example. The final concentrations are $1.1 \times 10^{-7}$M Compound III, $8.5 \times 10^{-8}$ to $1.0 \times 10^{-3}$M cholylglycine, $1.7 \times 10^{-9}$M acetylcholinesterase. After a 12 minute incubation at room temperature, the enzyme activity remaining in each sample cup is measured as described in Part B of this example. The results are shown in the following table:

| Cholylglycine in Serum (M) | Cholylglycine in Sample Cup (M) | Ad/5 Min. |
|---|---|---|
| $8.5 \times 10^{-7}$ | $8.5 \times 10^{-8}$ | $0.733 \pm 0.032$ |
| $1.8 \times 10^{-6}$ | $1.8 \times 10^{-7}$ | $0.733 \pm 0.016$ |
| $1.1 \times 10^{-5}$ | $1.1 \times 10^{-6}$ | $0.500 \pm 0.023$ |
| $1.1 \times 10^{-4}$ | $1.0 \times 10^{-5}$ | $0.204 \pm 0.016$ |
| $1.0 \times 10^{-3}$ | $1.0 \times 10^{-4}$ | $0.161 \pm 0.005$ |

C. The effectiveness of anticholylglycine antibody at modulating the activity of Compound III to inhibit acetylcholinesterase is determined as follows. Working solutions of phosphate-gel buffer, anticholylglycine antibody, Compound III, acetylcholinesterase and substrate are the same as those used in Part A of this example. Into the sample cups of the bichromatic kinetic analyzer, in the order listed, various amounts of phosphate-gel buffer, various amounts of antibody solution (listed in the following table), 2 μl of Compound III solution, and 10 μl of silicon oil to prevent evaporation.

After a five minute incubation at room temperature, 6 μl (0.06 units) acetylcholinesterase is added as described in Part B of this example. The total volume of reagents in each sample cup is 60 μl. The final concentrations are $1.1 \times 10^{-7}$M Compound III, and $2 \times 10^{-9}$M acetylcholinesterase. The results are listed in the following table:

| Anticholylglycine Antibody ($\mu l$) | Ad/5 Min. | Percent of Uninhibited Enzyme Signal |
| --- | --- | --- |
| 0 | 0.095 ± 0.004 | 8.5 |
| 2 | 0.480 ± 0.027 | 43 |
| 4 | 0.706 ± 0.084 | 63 |
| 6 | 0.856 ± 0.048 | 77 |
| 8 | 0.919 ± 0.018 | 82 |
| 10 | 0.890 ± 0.040 | 80 |
| 12 | 0.899 ± 0.020 | 80 |

EXAMPLE IV

To a solution of 5 g of 6-aminohexanol in 50 ml of methylene chloride at 0° C. is added dropwise 9.3 g of di-t-butyldicarbonate. The solution is allowed to come to room temperature and is stirred for 17 hours. The solution is washed with aqueous citric acid, aqueous sodium bicarbonate, and dried over anhydrous magnesium sulfate. The magnesium sulfate is filtered and the solvent evaporated to provide a yellow oil. The oil is purified on silica gel using 3% methanol in methylene chloride as eluent to provide N-t-butoxycarbonyl-6-aminohexanol having the following structural formula:

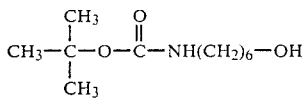

To 5.9 g of this compound and 3.06 g of triethylamine in 50 ml of methylene chloride is added 3.47 g of methanesulfonyl chloride. The solution is stirred for 30 minutes and washed with aqueous citric acid, aqueous sodium bicarbonate, and then dried over anhydrous magnesium sulfate. The magnesium sulfate is filtered and the solvent removed by evaporation to provide N-t-butoxycarbonyl-6-aminohexyl methanesulfonate. In 10 ml of dimethylformamide, without further purification, 6.2 g of this material is added to a solution of 2.5 g of β-mercaptoethanol in 60 ml of anhydrous dimethylformamide containing 3.5 g of potassium t-butoxide. The mixture is stirred for 17 hours at room temperature. The reaction mixture is poured into water and extracted with methylene chloride. The organic extract is washed with 100 ml of water three times and dried over anhydrous magnesium sulfate. The magnesium sulfate is filtered and the solvent is removed by evaporation. The residual oil is purified by silica gel chromatography using 5% methanol in methylene chloride as eluent to provide N-t-butoxycarbonyl-9-amino-3-thia-1-nonanol, having the formula:

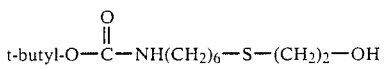

A solution of 2 g of this material and 1.4 g of diisopropylethylamine in 20 ml of methylene chloride is cooled to 0° C. and 1.64 g of methanesulfonic anhydride is added. After 30 minutes, 1.86 g of diisopropylethylamine and 2.0 g of O-ethyl methylphosphonothioic acid are added while keeping the reaction mixture at 0° C. The solution is allowed to come to room temperature over 30 minutes and then is refluxed for 2.5 hours. After cooling the product in methylene chloride, it is washed with aqueous sodium bicarbonate and dried over anhydrous magnesium sulfate. The magnesium sulfate is filtered and the solvent is removed by evaporation under reduced pressure. The crude product is purified by column chromatography using 1% methanol in methylene chloride as eluent to provide O-ethyl-S-(N-t-butoxycarbonyl-9-amino-3-thianonyl)methylphosphonothioate, having the following structural formula:

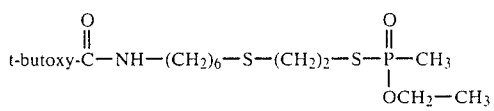

This compound, 250 mg, is stirred in a 2:1 mixture of methylene chloride and trifluoroacetic acid for 1 hour at room temperature. The solvent is removed by evaporation under reduced pressure. The resulting salt is dissolved in 6 ml of dioxane and 320 mg of diisopropylethylamine is added. Then 620 mg of the N-hydroxysuccinimide ester of N-acetyl-L-thyroxine is added and the mixture is stirred for 16 hours. The reaction mixture is poured into 50 ml of methylene chloride and washed successively with aqueous citric acid and aqueous sodium bicarbonate. The solution is dried over anhydrous magnesium sulfate. The magnesium sulfate is removed by filtration and the solvent is removed by evaporation under reduced pressure. The residual oil is chromatographed on silica gel using 1% methanol in methylene chloride as eluent. Recrystallization from acetonitrile provides 9-(ethoxymethylphosphinylthio)-7-thianonyl)-N-acetyl thyroxine amide, having the following structural formula:

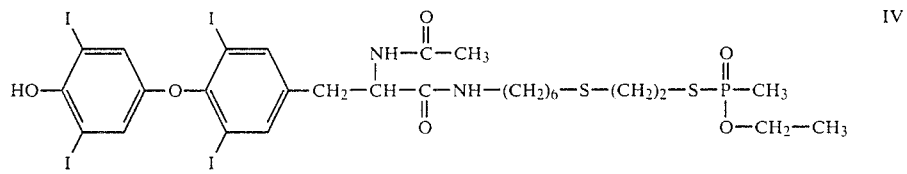

To a solution of 50 mg of this compound in 1.5 ml of methylene chloride is added 10.7 mg of methyl fluorosulfonate. A solid is formed over 2.5 hours. The solvent is decanted and the precipitate is triturated with anhydrous ether to provide a powder, which is the sulfonium salt of the formula:

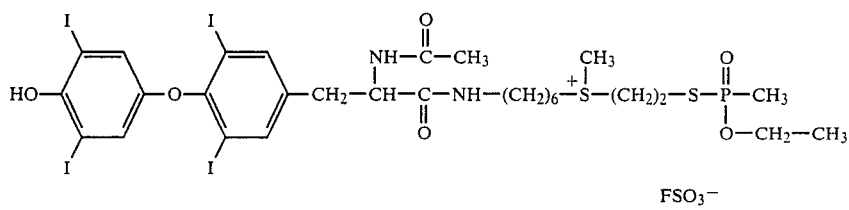

Rate constant for Compound V determined by the method set out in Example III-A is:

| | Second Order Rate Constant liters mole$^{-1}$min$^{-1}$ | Inhibitor Concentration |
|---|---|---|
| Compound V | $1.0 \times 10^8$ | $5.0 \times 10^{-9}$ M |

Thyroxine standard curve using Compound V.

Reagents:

A. A reagent containing 0.1 unit/ml ($1.4 \times 10^{-10}$M) of acetylcholinesterase (*E.electrius*) activity and $1 \times 10^{-8}$M in thyroxine IgG antibody, purified in a similar manner as previously described, in 0.1 molar phosphate buffer, pH 7.0 containing 0.1% gelatin, 1.0 mM N-methylorphenadrine, and 0.25 mM 8-anilino-naphthalene sulfonic acid.

B. The substrate reagent contains 1.0 mM of acetylthiocholine and 0.32 mM of DTNB in 0.1 molar pH 7.0 phosphate buffer.

C. A working solution of $2.5 \times 10^{-7}$M of Compound V in 0.1M phosphate-gel is prepared.

The assay is conducted by mixing 5 μl of serum containing varying amounts of thyroxine with 250 μl of reagent A. The mixture is incubated for five minutes at 37° C. To this solution are added 10 μl of reagent C and 250 μl of reagent B. Readings are taken at 5 minutes intervals using a bichromatic analyzer equipped with a 415/550 nm filter set.

| Serum Standard Curve | |
|---|---|
| Initial Conc. of Thyroxine in Serum (M) | ΔAd/5 Min. 415/550 nm |
| $0.6 \times 10^{-8}$ | 0.980 |
| $2.6 \times 10^{-8}$ | 0.927 |
| $5.2 \times 10^{-8}$ | 0.902 |
| $1.0 \times 10^{-7}$ | 0.793 |
| $2.1 \times 10^{-7}$ | 0.599 |
| $3.1 \times 10^{-7}$ | 0.578 |

Values for unknowns are determined from the standard curve.

Rate constant for Compound IV is determined by methods set out in Example III-A:

| | Second Order Rate Constant liters mole$^{-1}$min$^{-1}$ | Inhibitor Concentration |
|---|---|---|
| Compound IV | $3.5 \times 10^6$ | $2.5 \times 10^{-8}$ M |

Serum based standard curve for thyroxine is generated with Compound IV using a modification of the procedure described for Compound V.

Reagent A contains 1 mM N-methylorphenadrine and contains 7 mg/ml of sodium salicylate in phosphate-gel buffer, pH 7.0. The cholinesterase activity is 0.07 units/ml ($7 \times 10^{-11}$M) and the thyroxine antibody concentration is $1.4 \times 10^{-8}$M based on binding sites.

Reagent B is the same as Reagent B above.

Reagent C is a working solution of $5 \times 10^{-7}$M Compound IV in 0.1M phosphate-gel buffer.

The assay is performed using 10 μl of serum mixed with 250 μl of reagent A and 10 μl of reagent C. The mixture is incubated for 10 minutes at 37° C. before adding 250 μl of reagent B. The standard curve for determining unknowns is as follows:

| Initial Conc. of Thyroxine in Serum (M) | ΔAd/5 Min. |
|---|---|
| 0 | 0.646 |
| $5 \times 10^{-8}$ | 0.588 |
| $1.5 \times 10^{-7}$ | 0.525 |
| $3.1 \times 10^{-7}$ | 0.480 |
| $5 \times 10^{-7}$ | 0.518 |
| $1 \times 10^{-6}$ | 0.484 |
| $5 \times 10^{-6}$ | 0.426 |

EXAMPLE V

Following the above procedure of Example IV replacing 6-aminohexanol with 4-aminobutanol; 5-amino-3-thiapentanol; N-glycyl-6-amino-1-hexanol, respectively, provides

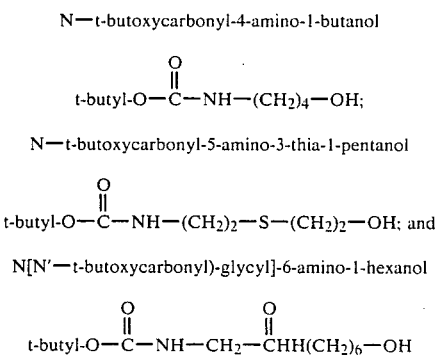

and these alcohols are in turn reacted with methanesulfonyl chloride, β-mercaptoethanol, methanesulfonic anhydride, and O-ethyl methylphosphonothioic acid, where appropriate, to provide inhibitor arms for coupling of the formula:

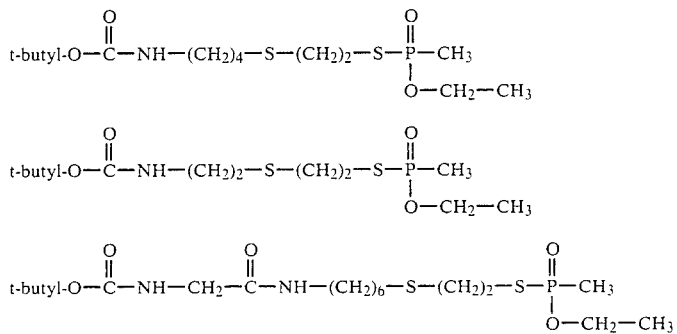

Alternately, O-butyl methylphosphonothioic acid is used to provide compounds such as

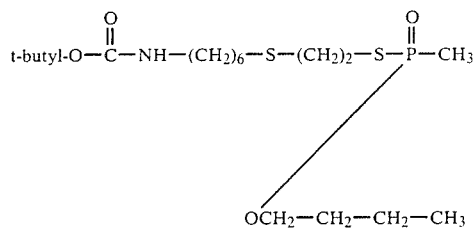

These intermediate reagents are deblocked and then reacted with the N-hydroxysuccinimide ester of N-acetyl-L-thyroxine to provide conjugates such as N-[12-(ethoxymethylphosphinylthio)-10-thia-3-aza-2-oxododecyl]-N$^\alpha$-acetylthyroxine amide, having the following formula:

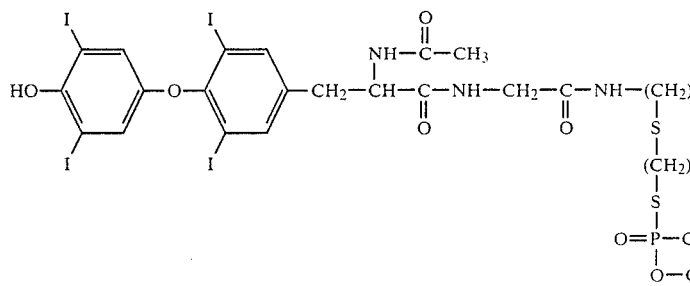

and the corresponding sulfonium salt, Compound VI. These compounds have second order rate constants of $2.5 \times 10^6$ and $1.7 \times 10^9$ liters mole$^{-1}$min$^{-1}$, respectively, at inhibitor concentration of $5 \times 10^{-8}$ molar and $2.5 \times 10^{-11}$ molar, respectively.

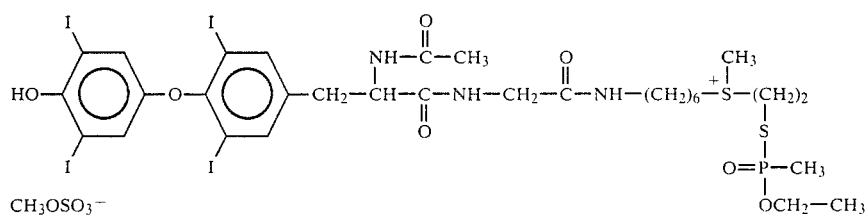

CH$_3$OSO$_3^-$ at room temperature, and poured into water. The resulting mixture is extracted with methylene chloride and the organic layer is washed with sodium chloride solution, dried over anhydrous magnesium sulfate. The magnesium sulfate is filtered and the solvent is removed by evaporation. The product is recrystallized from ethyl acetate/ether to provide N-(benzyloxycarbonyl)-6-amino-1-hexanol, mp 81.5°–83° C. having the following formula:

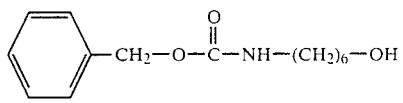

To 21 g of this compound in 100 ml of anhydrous pyridine is added 10.53 g of methanesulfonyl chloride at 0°–5° C. The reaction mixture is poured into cold water and extracted with ether. The ether solution was washed, dried, and the solvent removed to provide N-(benzyloxycarbonyl)-6-aminohexyl methanesulfonate as a waxy solid.

To a solution of 7.8 g of β-mercaptoethanol in 50 ml of dimethylformamide is added 5.15 g of sodium meth-

VI

EXAMPLE VI

A solution of 32 g of N-benzyloxycarbonyloxysuccinimide in 100 ml of tetrahydrofuran is reacted with 15 g of 6-amino-1-hexanol in 30 ml of 50% methanol:tetrahydrofuran. The reaction mixture is stirred overnight oxide with cooling in an ice bath. The entire yield is N-(benzyloxycarbonyl)-6-aminohexyl methanesulfonate from above in 150 ml of dimethylformamide is added to the β-mercaptoethanol solution in an inert atmosphere at 0° C. The mixture is stirred for 2 hours at room temperature and poured into a sodium chloride solution.

Extraction with methylene chloride, washing, and drying of the methylene chloride layer, followed by evaporation of the methylene chloride provides a solid. Recrystallization from ethyl acetate provides N-(benzyloxycarbonyl)-9-amino-3-thia-1-nonanol. A solution of 9.5 g of this compound in 160 ml of methanol containing 1.1 equivalents of concentrated hydrochloric acid and 9.5 g of palladium black is placed in a Parr hydrogenation apparatus. After 3 hours, the catalyst is filtered and the methanol removed to provide 9-amino-3-thia-1-nonanol hydrochloride, mp 69°–72° C.

To a solution of 3.49 mg, 12-acetyloxy-3-chloroformyloxy-14-hydroxycard-20(22)enolide (U.S. Pat. No. 3,981,982) in 60 ml of tetrahydrofuran is added 829 mg of N-hydroxysuccinimide and 0.988 ml of triethylamine at 0° C. After stirring for 3 hours at 0° C., the solid triethylamine hydrochloride is filtered and to the filtrate is added a solution of 1.5 g of 9-amino-3-thia-1-nonanol hydrochloride and 0.97 ml of triethylamine in 6.5 ml of methanol. The resulting mixture is stirred for 1 hour at room temperature and then partially evaporated under reduced pressure. The residue is diluted with aqueous sodium chloride and extracted with methylene chloride. The organic phase is washed, dried, and the solvent evaporated to afford a viscous liquid. Chromotography on silica gel using 2–4% methanol in methylene chloride provides 12-acetyloxy-3-[N-(9-hydroxy-7-thianonyl)carbamoyloxy]-14-hydroxycard-20(22)enolide.

To a solution of 2 g of this material in 15 ml of methanol is added 430 mg of pulverized anhydrous potassium carbonate. After stirring for 35 minutes at room temperature, the reaction mixture is diluted with excess chloroform, filtered through celite and the solvent partially evaporated under reduced pressure. The residue is dissolved in methylene chloride, washed successively with 0.1N hydrochloric acid and sodium chloride solutions, and dried over anhydrous magnesium sulfate. The magnesium sulfate is filtered and the solvent evaporated to provide a crude product. Chromatography on silica gel using methanol/methylene chloride as eluent provides 3-[N-(9-hydroxy-7-thianonyl)carbamoyloxy]-12,14-dihydroxycard-20(22)enolide.

To a solution of 0.725 g of the material in 3 ml of anhydrous tetrahydrofuran is added sequentially 0.265 ml of ethyl diisopropylamine and 0.265 g of methanesulfonic anhydride in 0.75 ml of tetrahydrofuran at −20° C. After stirring at −10° C. for 35 minutes, a solution of 0.784 g of dicyclohexylammonium O-ethyl methylphosphonothioate in 2 ml of methylene chloride is added to the mixture. Stirring for 5 hours at room temperature is followed by partitioning of the reaction mixture between methylene chloride and dilute hydrochloric acid. The organic phase is washed with sodium chloride solution, dried and the solvent evaporated to provide a crude product. Chromatography on silica gel using 2.5–5% methanol in methylene chloride as eluent provides 3-[N-[9-(ethoxymethylphosphinylthio)-7-thianonyl]carbamoyloxy]-12,14-dihydroxycard-20(22)enolide, having the following structural formula

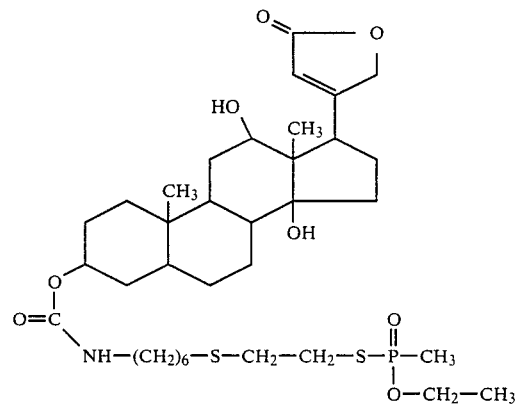

A mixture of 25 mg of this material is treated with 0.5 ml of methyl iodide and several drops of methylene chloride. After standing for 3 days in the dark, the solvent is removed by evaporation to provide the corresponding methyl sulfonium iodide, Compound VII, having the formula:

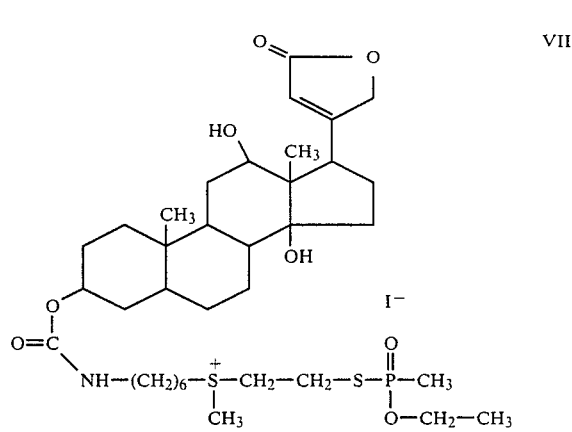

Following essentially the procedures set out in Example III, a serum standard curve is obtained from Compound VII. Commercial digoxin standards used in radioimmunoassay kits containing 0, 1, 2, 4 nanogram(ng)/ml of digoxin are used. The final concentration of digoxin antibody is $0.2 \times 10^{-9}$M, N-methylorphenadrine; $2.5 \times 10^{-3}$M and $1 \times 10^{-3}$M in the immunoreaction mixture and substrate mixture, respectively, to block serum pseudocholinesterase. The results for the standard curve are:

| Digoxin Standard | Ad/5 Minute |
|---|---|
| 0 | .639 |
| 0.5 ng/ml | .614 |
| 1.0 ng/ml | .583 |
| 2.0 ng/ml | .527 |
| 4.0 ng/ml | .462 |

From this standard curve, digoxin unknowns in serum samples can be determined.

EXAMPLE VII

A solution of 31.5 g of the N-hydroxysuccinimide ester of N-benzyloxycarbonylglycine [J. Am. Chem. Soc., 86, 1839, (1964)] in 100 ml of tetrahydrofuran is reacted dropwise with 12 g of 6-amino-1-hexanol in 50 ml of 50% methanol in tetrahydrofuran. The reaction is stirred for 12 hours at 23° C. and poured into water. The resulting precipitate is washed thoroughly with water, filtered, and dried to provide crude N-(benzyloxycarbonylglycyl)-6-amino-1-hexanol. The pure compound recrystallized from ethyl acetate has a melting point of 104°–5° C.

A solution of 15 g of this compound in 70 ml of pyridine is cooled in an ice bath and 4.17 ml of cold methanesulfonyl chloride is added over a 5 minute period. After stirring for 2 hours at 0°–5° C., the reaction mixture is poured into ice cold water and the resulting precipitate collected by filtration. The solid is recrystallized from ethyl acetate/hexane to provide N-(benzyloxycarbonylglycyl)-6-aminohexyl methanesulfonate, mp 82°–83° C.

A solution of 16.5 g of this compound in 75 ml of dimethylformamide is added to a cold solution of 4.0 g of β-mercaptoethanol in 25 ml of dimethylformamide containing 2.65 g of sodium methoxide in an inert atmosphere. The reaction is stirred for 2 hours at room temperature and poured into sodium chloride solution. Extraction of this solution with methylene chloride and a standard washing, drying and evaporation work-up provides N-(benzyloxycarbonylglycyl)-9-amino-3-thia-1-nonanol. Recrystallization from ethyl acetate provides the pure compound melting at 99°–100° C.

A solution of 1.15 g of this alcohol in 7 ml of chloroform is treated with 0.387 g of thionyl chloride. The mixture is stirred for 1.5 hours at room temperature and volatiles are evaporated at reduced pressure. A solution of 1.04 g of the residual solid in 3 ml of dimethylformamide is added to a solution of sodium O-ethyl methylphosphonothioate (prepared from 2.69 mM of sodium hydride and 0.377 g of O-ethyl methylphosphonothioic acid) in 1 ml of dimethylformamide. After stirring for 16 hours at 60° C., the mixture is poured into sodium chloride solution and extracted with methylene chloride. The organic phase is washed, dried, and the solvent removed to provide an oil. Chromatography on silica gel using 2–4% methanol in methylene chloride provides O-ethyl-S-[N-(benzyloxycarbonylglycyl)-9-amino-3-thianonyl]methyl phosphonothioate, having the following structural formula:

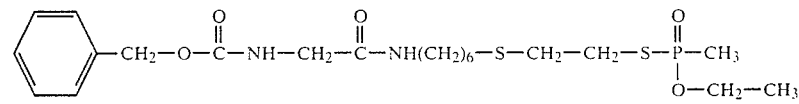

A solution of 6 g of N-benzyloxycarbonylglycyl-9-amino-3-thia-1-nonanol in 100 ml of methanol containing 1.1 equivalents of concentrated hydrochloric acid and 6 g of palladium black is hydrogenated in a Parr apparatus for 2 hours. Filtration of the palladium catalyst and evaporation of the solvent provides N-glycyl-9-amino-3-thia-1-nonanol hydrochloride, having the formula:

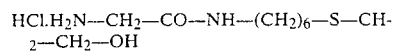

To a stirred suspension of 5 g of sodium diphenylhydantoin in 35 ml of dry dimethylformamide is added 3.04 g of ethyl bromoacetate. The mixture is stirred for 3 hours at room temperature and the dimethylformamide is evaporated at reduced pressure. The residue is distributed between methylene chloride and sodium chloride solution. The organic phase is washed, dried, and the solvent is removed to provide the N-alkylated diphenylhydantoin derivatives, mp 179°–180° C. To 4.5 g of this compound in 50 ml of tetrahydrofuran is added 2.17 g of potassium hydroxide in 15 ml of water. The mixture is stirred for 12 hours and the solvent is removed under reduced pressure. The residue is diluted with 35 ml of water and the aqueous solution extracted with ether. The aqueous solution is acidified with 6N hydrochloric acid to precipitate 2-(N-diphenylhydantoinyl)acetic acid.

To a solution of 1.25 g of this compound and 0.500 g of N-hydroxysuccinimide in 5 ml of 40% tetrahydrofuran in dimethylformamide is added 0.906 g of dicyclohexylcarbodiimide and the reaction is cooled. After stirring for 3 hours at room temperature, the dicyclohexylurea is filtered and to the filtrate is added 1.09 g of N-glycyl-9-amino-3-thia-1-nonanol hydrochloride and 0.41 g of triethylamine. The reaction is stirred for 12 hours at room temperature and then partitioned between methylene chloride and saturated sodium chloride solution. The organic layer is washed, dried, and the solvent is evaporated to provide an oil. Chromatography on silica gel provides 12-[2-(N-diphenylhydantoinyl)acetamido]-11-oxo-10-aza-3-thia-1-dodecanol, having the following structural formula:

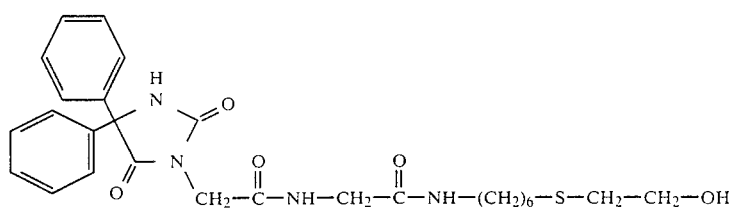

This compound is reacted with sodium O-ethyl methylphosphonothioate by methods described earlier in this example to provide O-ethyl-S-[12-[2-(N-diphenylhydantoinyl)acetamido]-11-oxo-10-aza-3-thiadodecyl]-methyl phosphonothioate, having the following structural formula:

VIII

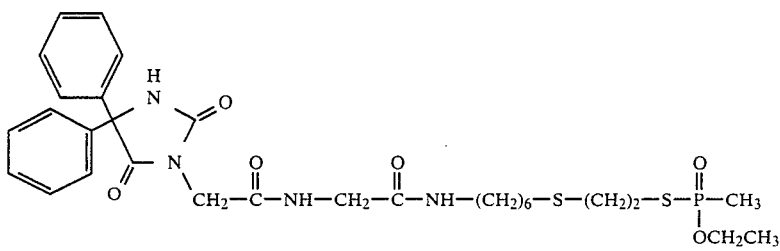

A solution of 0.512 g of this material and 0.119 g of dimethylsulfate in 1 ml of tetrahydrofuran is heated at 65°–70° C. for 6 hours under an inert atmosphere. The solvent is removed at reduced pressure. The residue is taken up in chloroform and a precipitate is obtained by the addition of ethyl ether to provide O-ethyl-S-[12-[2-(N-diphenylhydantoinyl)acetamido]-11-oxo-10-aza-3-thiadodecyl]methylphosphonothioate methylsulfate having the formula:

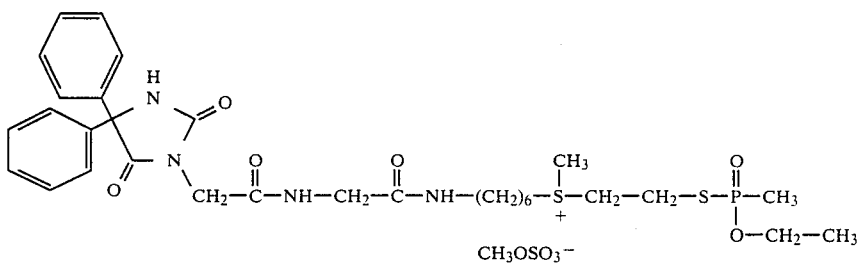

CH$_3$OSO$_3^-$

Compounds VIII and IX have second order rate constants for the inhibition of acetylcholinestrase determined by previously described methods of $6.8 \times 10^5$ liters mole$^{-1}$ min$^{-1}$ and $1.4 \times 10^9$ liter mole$^{-1}$ min$^{-1}$, respectively. This inhibition is modulated by dilantin antibody. A typical standard curve in buffer for Compound IX is:

| Dilantin Conc. moles/liters | mAd/5 Min. |
|---|---|
| 0 | 83.5 |
| 10$^{-7}$ | 74.1 |
| 10$^{-6}$ | 52.5 |
| 10$^{-5}$ | 47.2 |

EXAMPLE VIII

Following the procedures of Example VII using ethyl 4-bromobutyrate provides 4-(N-diphenylhydantoinyl)butyric acid, mp. 147°–148° C.

The N-hydroxy-5-norbornene-2,3-dicarboximide ester of N-carbobenzyloxy-β-alanine, [Chem. Pharm. Bull., 22, 1857 (1974)], (15.88 g) is condensed with 5 g of 5-amino-3-thia-1-pentanol using previously described procedures to provide 9-benzyloxycarbamido-7-oxo-6-aza-3-thia-1-nonanol, mp 99°–101° C. Hydrogenation of this material provides 9-amino-7-oxo-6-aza-3-thia-1-nonanol hydrochloride.

HCl.NH$_2$—CH$_2$—CH$_2$—CO—NH—CH$_2$—CH$_2$—S—CH$_2$—CH$_2$—OH

IX

This material is condensed with 4-N-(N-diphenylhydantoinyl)butyric acid by previously described techniques and the product reacted with sodium O-ethyl methylphosphonothioate to provide a conjugate of the formula

X

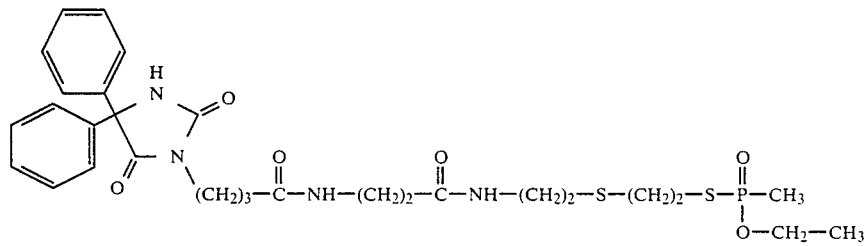

Conjugate X has a second order rate constant for the inhibition of acetylcholinesterase of $2.2 \times 10^6$ liters mole$^{-1}$ min$^{-1}$. This inhibition is modulated in the presence of dilantin antibody. A standard curve can be prepared to permit the determination of dilantin in serum samples.

EXAMPLE IX

To 204 mg of O-ethyl-S-[5-(t-butoxycarbonylamino)-3-thiapentyl]methylphosphonothioate is added 20 ml of 50% methylene chloride-trifluoroacetic acid and the mixture is stirred at room temperature for 1 hour. The solvent is evaporated and a toluene azeotrope used to remove residual trifluoroacetic acid. The residue is dissolved in 2.0 ml of dimethylformamide, and 83 μl of triethylamine, 140 mg of 6-(3-theophylline)hexanoic acid, prepared by the method of W. Traube, Ber., 36, 3035 (1900), 140 mg of hydroxybenztriazole, 113 mg of dicyclohexylcarbodiimide, and 1 ml of dimethylformamide, are added. The reaction mixture is stirred at room temperature for 6 hours and the solvent removed by evaporation at reduced pressure. The residue is dissolved in methylene chloride, washed with sodium bicarbonate, saturated sodium chloride, and dried over anhydrous magnesium sulfate. The magnesium sulfate is removed by filtration and the solvent is removed by evaporation. The residue is purified by chromatography on silica gel using 10% methanol in methylene chloride as eluent to provide N-[2-[2-(ethoxymethylphosphinylthio)ethylthio]ethyl]-1-methyl-2,6-dioxo-1,2,3,6-tetrahydro-7H-purine-3-hexanamide, mp 103°–106° C. and having the following formula:

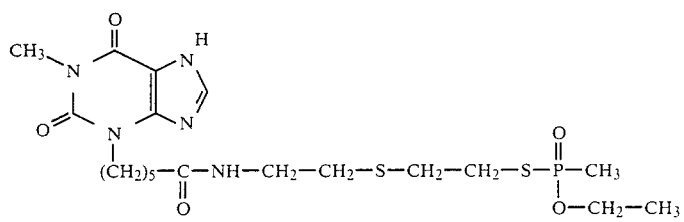

This compound has a second order rate constant for the inhibition of acetylcholinesterase of $5.5 \times 10^6$ liter mole$^{-1}$ min$^{-1}$. This inhibition is modulated by theophylline antibody. This compound is used to determine theophylline in blood serum by methods previously described.

What is claimed is:

1. An analytical reagent for determining ligands in test samples comprising ligand analog-irreversible enzyme inhibitor conjugate.

2. An analytical reagent according to claim 1 wherein the irreversible enzyme inhibitor is an organophosphorous irreversible enzyme inhibitor of acetylcholinesterase.

3. An analytical reagent according to claim 1 having the formula:

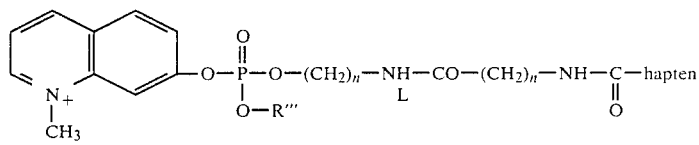

wherein n is 2–8 and R' and R" are alkyl having 1–10 carbon atoms, and B' is —S or the sulfonium salt thereof.

4. A compound according to claim 3 wherein R' and R" are alkyl having 1–4 carbon atoms and n is 2–6.

5. An analytical reagent having the formula

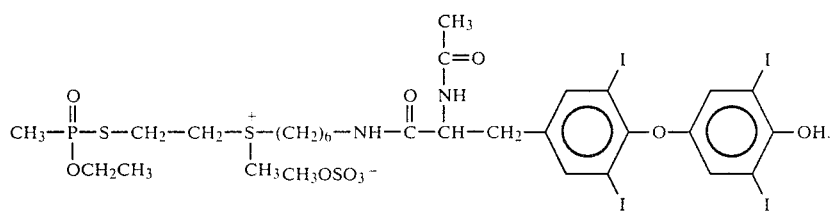

wherein R'" is alkyl having 1–10 carbon atoms and n is 2–8, and L is a biologically compatible counter ion.

6. An analytical reagent according to claim 1 which is

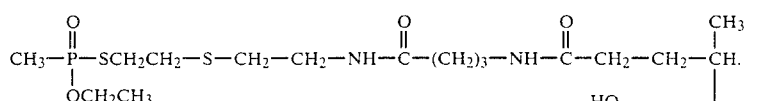

7. An analytical reagent according to claim 1 which is

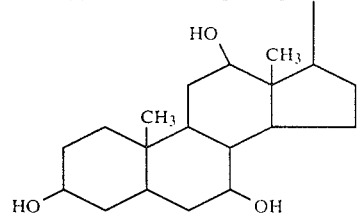

8. An analytical reagent according to claim 1 which is
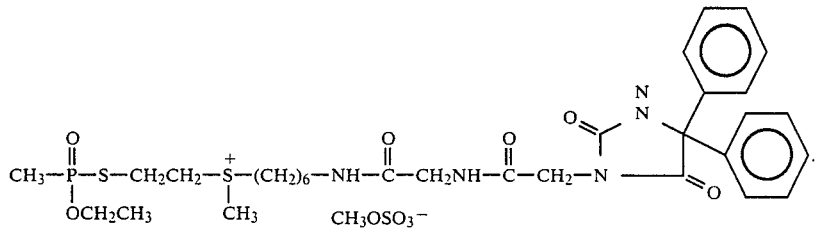
9. An analytical reagent according to claim 1 which is
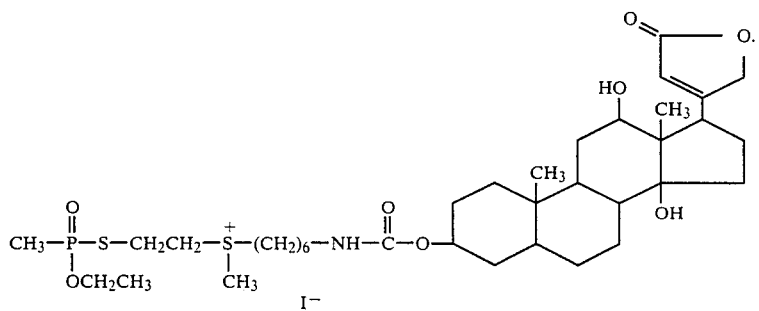
10. An analytical reagent according to claim 1 which is
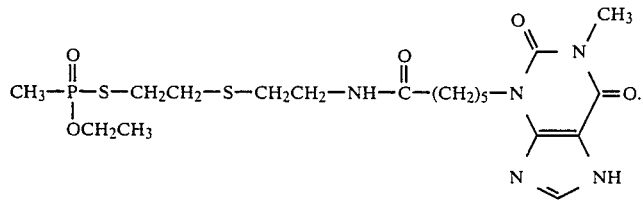
11. An analytical reagent according to claim 1 which is
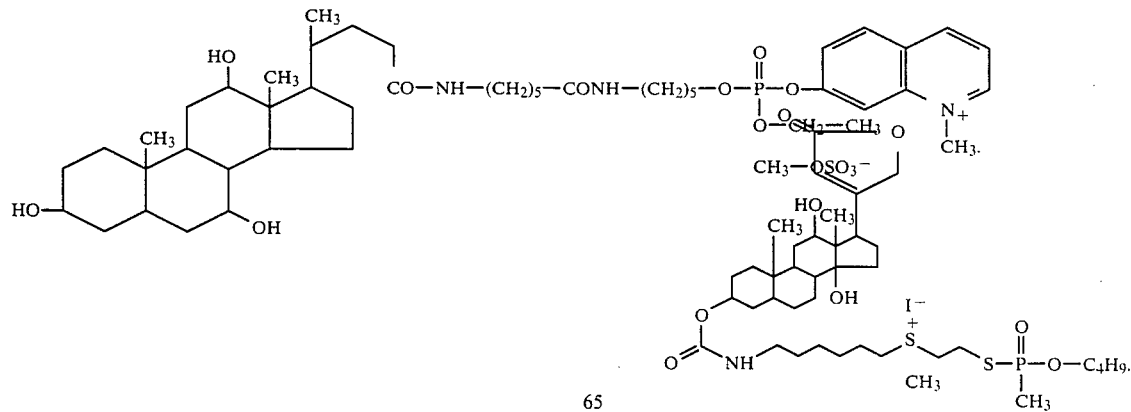
12. An analytical reagent according to claim 1 which is
13. An analytical reagent according to claim 1 which is

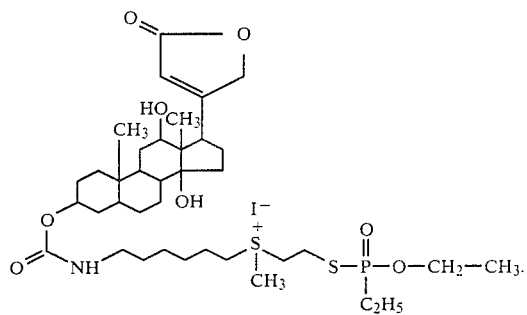
14. An analytical reagent according to claim 1 which is
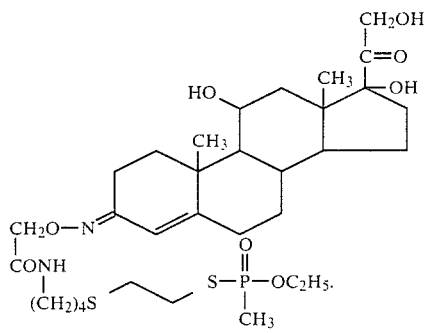
17. An analytical reagent according to claim 1 which is
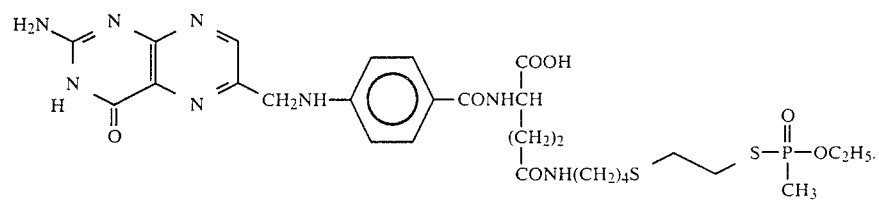
15. An analytical reagent according to claim 1 which is
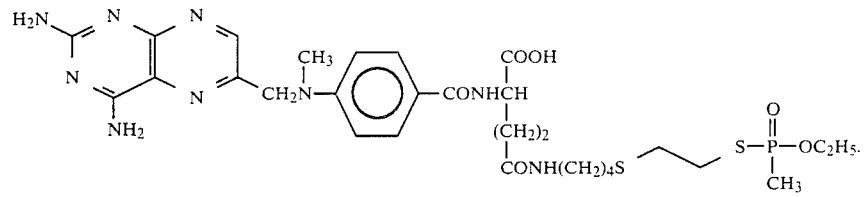
16. An analytical reagent according to claim 1 which is
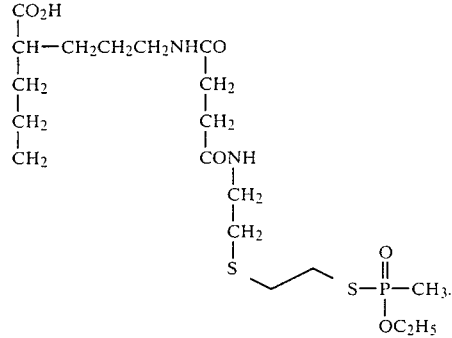
18. An analytical reagent according to claim 1 which is
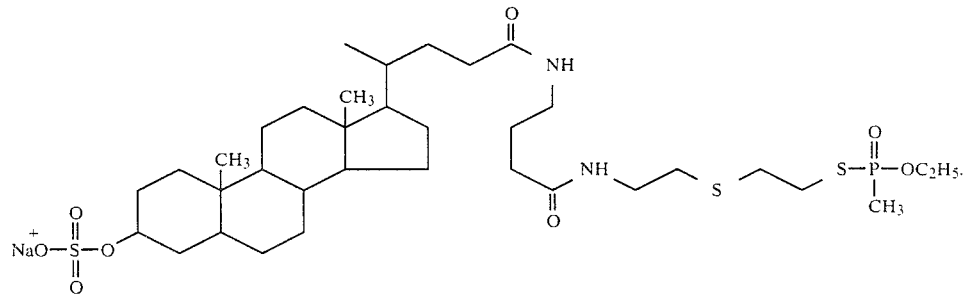

19. An analytical reagent according to claim 1 which is

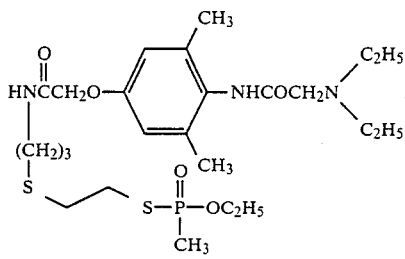

20. An analytical reagent according to claim 1 which is

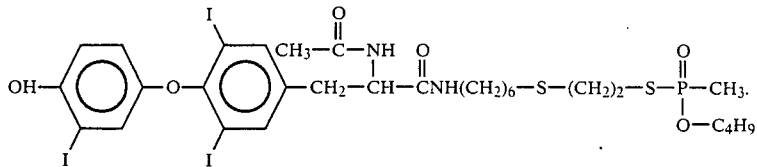

21. An analytical reagent according to claim 1 which is (gentamicin amino group)

-continued

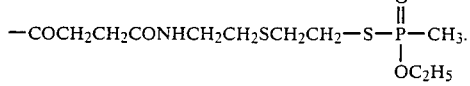

22. An analytical reagent according to claim 1 which is

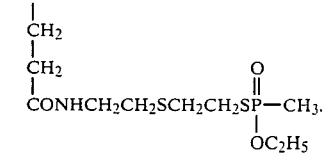

(amino group of tobramycin)

23. An analytical reagent according to claim 1 which is

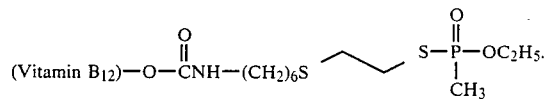

24. An analytical reagent according to claim 1 which is

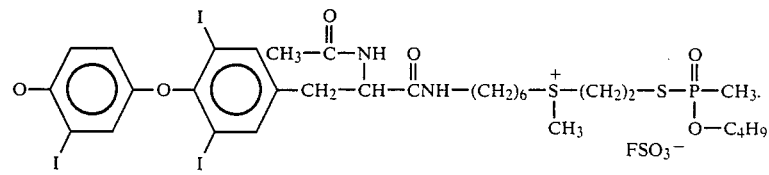

25. An analytical reagent which is:

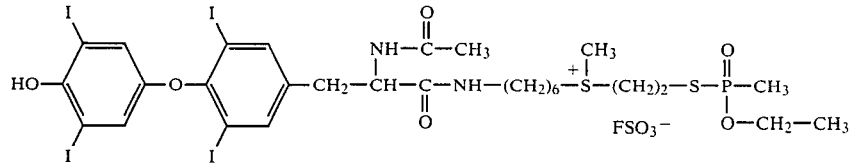

* * * * *